(12) United States Patent
Martinez Torrecuadrada et al.

(10) Patent No.: US 9,062,109 B2
(45) Date of Patent: Jun. 23, 2015

(54) ANTI-EPHRIN-B2 ANTIBODY AND COMPOSITIONS COMPRISING IT

(75) Inventors: Jorge Luis Martinez Torrecuadrada, Madrid (ES); Maria Angeles Abengozar Infantes, Madrid (ES)

(73) Assignee: Fundacion Centro Nacional De Investigaciones Oncologicas (CNIO), Madrid (ES)

( * ) Notice: Subject to any disclaimer, the term of this patent is extended or adjusted under 35 U.S.C. 154(b) by 0 days.

(21) Appl. No.: 13/824,171

(22) PCT Filed: Sep. 20, 2011

(86) PCT No.: PCT/ES2011/070655
§ 371 (c)(1),
(2), (4) Date: Jun. 13, 2013

(87) PCT Pub. No.: WO2012/038573
PCT Pub. Date: Mar. 29, 2012

(65) Prior Publication Data
US 2013/0287795 A1    Oct. 31, 2013

(30) Foreign Application Priority Data

Sep. 21, 2010    (ES) .................................. 201031402

(51) Int. Cl.
| | | |
|---|---|---|
| *A61K 39/00* | (2006.01) | |
| *A61K 39/395* | (2006.01) | |
| *C07K 16/28* | (2006.01) | |

(52) U.S. Cl.
CPC ............. *C07K 16/28* (2013.01); *C07K 2317/73* (2013.01); *C07K 2317/92* (2013.01); *A61K 2039/505* (2013.01); *C07K 2317/33* (2013.01); *C07K 2317/622* (2013.01); *C07K 2317/76* (2013.01)

(58) Field of Classification Search
None
See application file for complete search history.

(56) References Cited

U.S. PATENT DOCUMENTS 7,696,330 B2 *    4/2010    Meulen et al. ............. 530/388.8

FOREIGN PATENT DOCUMENTS

| WO | WO2007053718 | * | 5/2007 | ............. C07K 16/30 |
| WO | 2007127506 A2 | | 11/2007 | |
| WO | 2010019565 A2 | | 2/2010 | |

OTHER PUBLICATIONS

PubMed search for Ephrin B2, retrieved on Apr. 18, 2014.*
Hai U. Wang; Molecular Distinction and Angiogenic Interaction between Embryonic Arteries and Veins Revealed by ephrin-B2 and its Receptor Eph-B4, Cell, vol. 93, pp. 741-753, May 29, 1998.
Gavin Thurston; Role of Angiopoietins and Tie receptor tyrosine kinases in agniogenesis and lymphangiogenesis, Cell Tissue Res (2003) 314:61-68.
Ralf H. Adams; Molecular regulation of angiogenesis and lymphangiogenesis, Nature, Jun. 2007, vol. 8, pp. 464-478.
Taija Makinen; PDZ interaction site in ephrin B2 is required for the remodeling of lymphatic vasculature, Genes Dev. 2005 19: 397-410.
Tuomas Tammela; Lymphangiogenesis: Molecular Mechanisms and Future Promise, Cell, 2010 140, pp. 460-476.
Ralf H. Adams; Eph Receptors and Ephrin Ligands: Essential mediators of Vascular Development, Trends Cardiovascular Med, vol. 10, No. 5, 2000, pp. 183-188.
Werner Risau; Mechanisms of angiogenesis, Nature, vol. 386, pp. 671-674, Apr. 17, 1997.
Yingdi Wang; Ephrin-B2 controls VEGF-induced angiogenesis and lymphangiogenesis, Nature, vol. 465, pp. 483-486, May 27, 2010.
Suphansa Sawamiphak; Ephrin-B2 regulates VEGFR2 function in developmental and tumour angiogenesis, Nature, vol. 465, pp. 487-491, May 27, 2010.
Ralf H. Adams; Roles of ephrinB ligands and EphB receptors in cardiovascular development: demarcation of arterial/venous domains, vascular morphogenesis, and sprouting angiogenesis, Genes & Development 13:295-306, 1999.

* cited by examiner

*Primary Examiner* — Elly-Gerald Stoica
(74) *Attorney, Agent, or Firm* — McNees Wallace & Nurick LLC

(57) ABSTRACT

The present invention relates to a novel antibody against ephrin B2 and its use to detect the protein and as a medicament for inhibiting angiogenesis and lymphangiogenesis in the treatment of diseases in which these processes are implicated, for example, cancer.

10 Claims, 13 Drawing Sheets

A

B

A

B

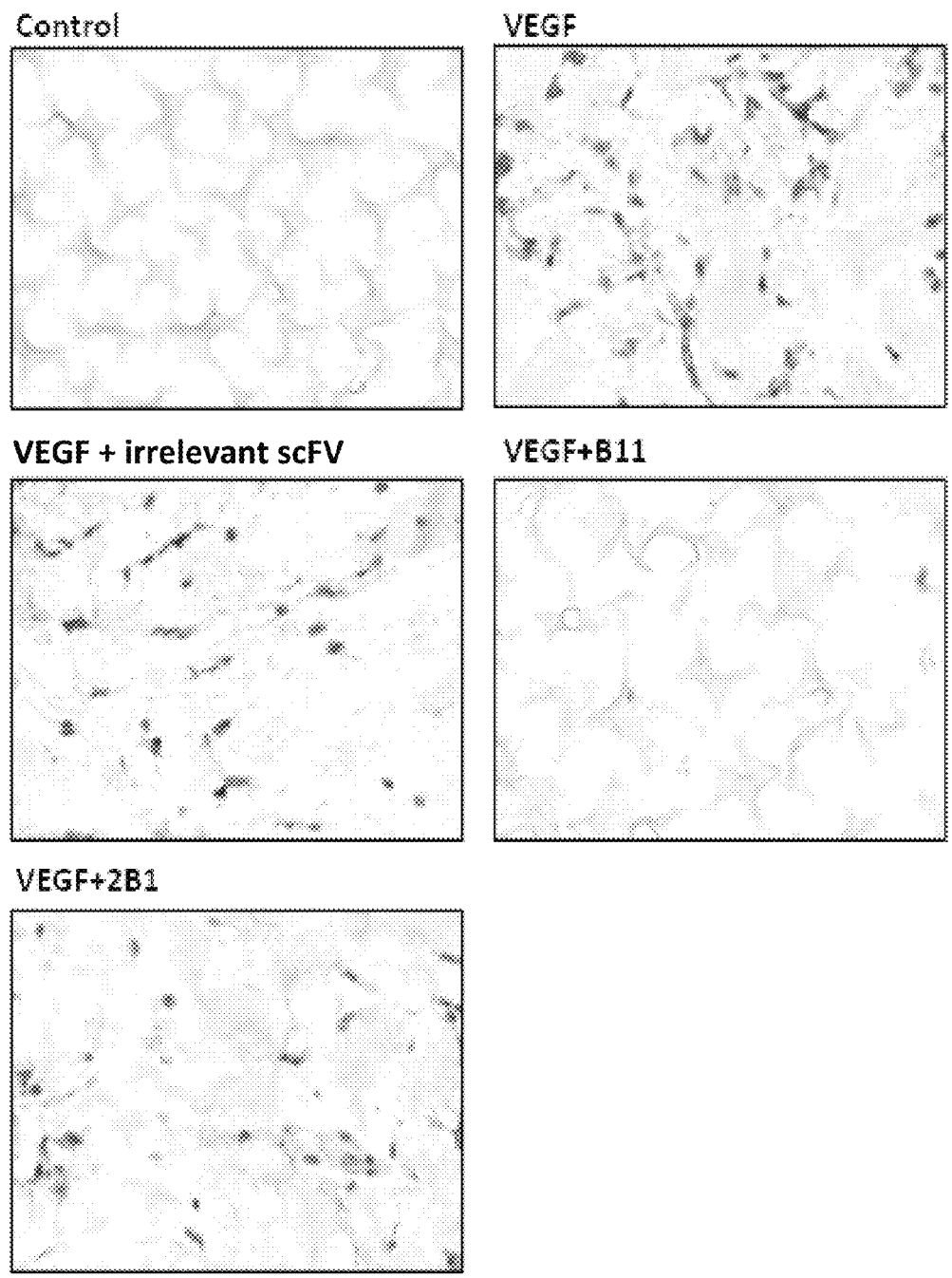

ANTI-EPHRIN-B2 ANTIBODY AND COMPOSITIONS COMPRISING IT

PRIORITY

This application is a national stage application for PCT Patent Application PCT/EP2011/070655, titled "ANTI-EPHRIN-B2 ANTIBODY AND USE THEREOF," filed Sep. 20, 2011, which is hereby incorporated by reference in its entirety.

REFERENCE TO A SEQUENCE LISTING

This application contains a Sequence Listing in computer readable form. The computer readable form is incorporated herein by reference.

The present invention belongs to the field of Biomedicine and Biotechnology and relates to a new ephrin B2 specific antibody capable of blocking the formation of blood vessels (angiogenesis) and lymphatic vessels (Lymphangiogenesis). Furthermore, the present invention relates to the use of the mentioned antibody, for example, for the preparation of a medicament.

STATE OF THE ART

Angiogenesis, or new blood vessel formation from pre-existing ones plays a key role in numerous physiological processes during embryonic development and postnatal life: reproduction, scarring and inflammation. Although the molecular mechanisms responsible for the transition of an endothelial cell to an angiogenic phenotype are not completely known, it is a complex process that involves the proliferation, migration and assembly of endothelial cells, followed by the recruitment of other perivascular cells such as pericytes or muscle cells and the remodelling of the extracellular matrix (Risau, W. Nature 1997, 386:671-674). The uncontrolled growth of blood vessels is an underlying disorder in numerous pathologies such as rheumatoid arthritis or diabetic retinopathy, and especially neoplastic processes. Tumour growth will depend on the constant supply of oxygen and nutrients through the formation of a network of new blood vessels, such that in the absence of adequate vascularisation, cells undergo a process of necrosis and/or apoptosis that inhibits or moderates the increase of tumour volume.

In addition to blood vessels, the vertebrate circulatory system is comprised of lymphatic vessels that also play a critical role during the organism development and pathological processes. The lymphatic system drains the interstitial fluid of the tissues and drives it to the blood system, also absorbs lipids from digestive system, is part of the individual immune defense transporting cells of the immune system, for example in inflammation, and in various pathological conditions induces types of lymphedema, inflammatory diseases and is involved in the invasion and metastasis of carcinomas (Tammela, T. and Alitalo, K. Cell 2010, 140:460-76). The study of lymphangiogenesis or formation of lymphatic vessels from pre-existing ones, remained delayed for many decades and it is not until recent years that have been described biomolecular mechanisms and specific markers, which are currently being used to study the process of tumor dissemination and metastasis.

During embryonic development, the blood vessels are originated from endothelial precursors derived from mesoderm in a process called vasculogenesis, whereas the formation of lymphatic vessels seems to be initiated from a set of venous endothelial cells from the jugular region and perimesonephric. Because their common embryonic origin, both vascular systems share similar molecular mechanisms that regulate their development and maturation. Several signalling pathways have been identified in which tyrosine kinase receptors play a very important role in these mechanisms of formation of cardiovascular system, in particular, the vascular endothelial growth factor (VEGF) signalling pathway through their corresponding receptors (VEGFR) in cooperation with the activity of Tie-1 and Tie-2 receptors regulated by angiopoietins (Thurston, G., Cell Tissue Res 2003; 314:61-68). Furthermore, it has been shown that another group of molecules, the ephrins (acronym for "producing hepatoma erythropoietin receptor interactors"), along with their corresponding receptors (Eph), is also involved in the remodelling of blood vascular system (Adams, R H and Klein, R. Trends Cardiovasc Med 2000, 10: 183-188) and lymphatic system (Mäkinen, T et al. Genes Dev 2005, 19:397-410). This family includes the largest known group of tyrosine kinases, with 14 receptors and 8 ligands and is subdivided into two receptor categories, Eph A and Eph B, based on their sequence homology and binding properties of the corresponding ligands. The EphA receptors bind ligands of the subgroup ephrin A, characterized by being anchored to the membrane by a glycosylphosphatidylinositol (GPI) molecule, while the Eph B receptors bind ligands of the subgroup ephrin B which are anchored to the membrane through a transmembrane region followed by a cytoplasmic domain. It has been reported that arteries express the transmembrane ligand ephrin B2 and veins express Eph B4 receptor (Adams, R H and Alitalo K. Nat Rev Mol. Cell. Biol 2007, 8: 464-478).

This group of molecules is responsible for regulating diverse cellular functions such as morphology, migration, repulsion, cell adhesion and invasion by modifying the organization of the cytoskeleton and influencing the activity of integrins and other intracellular adhesion molecules (Pasquale, E B. Cell 2008, 133:38-52). These activities are dependent on the interaction of the Eph receptors expressed in a cell with the corresponding ephrin expressed in another cell, generating bidirectional signals affecting each of the cells involved. The signalling coming from Eph receptor is called "forward" and depends on a tyrosine kinase domain located on its cytoplasmic region, which has the ability to phosphorylate itself and to phosphorylate other proteins, and on the association of the receptor with other effector molecules. For its part, the ligand ephrin B generates another signal called "reverse" which depends, on one hand, on the phosphorylation of several tyrosine in its cytoplasmic region, carried out by Src family kinases and other tyrosine kinase receptors, and, on the other hand, other associated proteins. Furthermore, most of the Eph receptors and ephrins B have a binding site to PDZ domains in their cytoplasmic regions, which are important to perform the physiological functions, particularly of the ephrins B (Mäkinen, T et al. Genes Dev 2005; 19:397-410).

Studies on the inactivation of genes coding for Eph B4 and ephrin B2 in transgenic mice suggest a fundamental role of both proteins in the development of the vascular system. Deficient mice on these genes have an altered angiogenesis which is lethal in embryonic stage (Wang, H U et al. Cell 1998, 93:741-753; Adams, R H et al. Genes Dev 1999, 13:295-306), while the study of mice expressing ephrin B2 with mutations in signaling active sites, showed that this protein controls lymphoangiogenic and angiogenic growth through regulation of VEGF signalling pathway (Wang, Y et al. Nature 2010, 465: 483-6; Sawamiphak S et al. Nature 2010, 465:487-91).

In WO2007/127506 and WO2010/019565 are described ephrin B2 antibodies. In WO2007/127506 it is shown that the described antibodies block signalling between ephrin B2 and Eph B4 and have an inhibiting effect in angiogenesis, capable of reducing tumour volume in an animal model.

However, the need for new therapeutic agents able to control angiogenesis continues to exist.

DESCRIPTION OF THE INVENTION

The present invention provides a novel therapeutic agent capable of controlling angiogenesis and relates to a novel antibody against ephrin B2, with a sequence distinct from the antibodies described to date and with a high specificity, capable of inhibiting the formation of new blood and lymph vessels and significantly prevents the growth of tumours. The ephrin B2 antibodies described in WO2007/127506 are able to inhibit angiogenesis but it is not described an inhibitory effect of linfoangiogenesis.

The present invention is based on antibodies that recognize and specifically bind to ephrin B2 and refers to the mentioned antibodies and methods and compositions based on them, which constitute an important diagnostic and therapeutic tool against those pathologies associated with ephrin B2.

In a first aspect, the present invention relates to novel antibodies against ephrin B2 that have antiangiogenic and antilymphangiogenic activity and are capable of inhibiting the growth of solid tumours.

This invention provides a new solution to the problem of controlling diseases involving angiogenesis disorders, as is, for example, cancer.

As demonstrated by the inventors, the B11 antibody described here specifically recognizes ephrin B2 so that inhibits its binding to the Eph B4 receptor which, on in vitro assays, inhibits the formation of tubules and the migratory capacity of endothelial cells (HUVEC) and, on in vivo assays, with cells of pancreas, lung and colon carcinoma, produces a considerable reduction in the number of blood and lymphatic vessels in the tumours. Furthermore, the inventors have found that the antibody of the present invention is able to significantly delay the tumour growth and induce size reduction thereof. The inventors have shown that B11 antibody blocked the interaction of the ephrin B2 to Eph B4 both in vitro and in cultured cells, which also shows how the antibody is capable of inhibiting ephrin signalling through its receptor (see FIG. 5 herein).

The 2B1 antibody is also capable of inhibiting the formation of tubules and the migratory capacity of endothelial cells (HUVEC) and reduces the number of blood and lymphatic vessels in tumours on in vivo assays. The 2B1 antibody does not compete with the Eph B4 receptor in Biacore™ assays and neither in cellular assays of Eph B4 blockage, as shown in FIG. 5 herein.

Therefore, a first aspect of the present invention relates to an isolated polypeptide that:
a. comprises an amino acid sequence with at least 76% sequence identity with SEQ ID NO: 1 and
b. specifically recognizes and binds to ephrin B2.

Preferably, the polypeptide comprises an amino acid sequence with at least 80%, 85%, 90%, 95%, 99% identity with SEQ ID NO: 1. More preferably, the polypeptide comprises the amino acid sequence SEQ ID NO: 1.

The term "isolated" as used in this description, referring to a polypeptide means that the polypeptide has been identified and separated and/or extracted from a natural environment.

The term "% sequence identity" with respect to a polypeptide, refers to the percentage of amino acid of the sequence in question that are identical to the amino acid of the sequence that is compared, after aligning the sequences and introducing spaces, if necessary, to achieve the maximum percentage of identity of the sequences, without taking into account the conservative substitutions. The alignment can be performed in different ways, known to those skilled in the art, for example using public tools such as BLAST, BLAST-2, ALIGN or Megalign (DNASTAR). A person skilled in the art can determine the appropriate parameters for measuring the alignment, including any needed algorithms to achieve maximal alignment of the sequences being compared.

The term "ephrin B2", as used in this description refers, unless specifically or contextually otherwise indicated, to any native polypeptide or any variant of the ephrin B2 protein. The name of this protein is an acronym for "erythropoietin producing hepatoma receptor interactors", but may also be called ephrin. A naturally occurring polypeptide can be a naturally truncated or secreted form, such as the extracellular domain, or any naturally occurring variant such as the various alternative "splicing" forms or any allelic variant.

Preferably, the polypeptide is an antibody. More preferably, the antibody is human. Preferably, the human antibody isotype is IgG1, IgG2, IgG3, IgG4, or IgA.

The terms "antibody" or "immunoglobulin" are used in its broadest sense and include monoclonal antibodies, polyclonal antibodies, multispecific (as long as they exhibit the desired biological activity) and may include antibody fragments.

The antibody can be human, humanized and/or affinity matured. A "human antibody" is one whose amino acid sequence corresponds to that of an antibody produced by a human.

The antibodies of the present invention can be single chain variable fragments (scFv, English "single chain variable Fragment"). The term "variable" refers to the fact that certain portions of the variable domains of antibodies are quite different in their sequence, and are the sequences responsible for specific binding of each antibody to its antigen. However, the variability is not evenly distributed along the entire variable domain of the antibody. This variability is concentrated in three segments called CDR (English, "complementarity-determining regions") or hypervariable regions, found in the variable domains of both the light chain and heavy chain. The most conserved portions of variable domains are called the framework. The CDRs from the two chains (heavy and light) contribute to the formation of the antigen binding site. The variable fragment or "Fv" is the minimum antibody fragment which contains a complete antigen recognition and binding site. A single chain variable fragment may have a heavy chain variable domain and a light chain variable domain covalently linked by a peptide which permits that heavy and light chains can associate to form the structure of the antigen binding site. An Fv can also be formed by two chains. In any case, even a single variable domain with only three CDRs, is sufficient to recognize and specifically bind an antigen, although with lower affinity.

The light chains of antibodies or vertebrates immunoglobulins can be of two types, called kappa and lambda, depending on the amino acid sequences of their constant domains. Depending on the amino acid sequences of the constant domains of the heavy chains, immunoglobulins are grouped in different classes or types. There are five main types or classes: IgA, IgD, IgE, IgG and IgM. Furthermore, some of them are divided into subclasses or isotypes, such as IgG1, IgG2, IgG3, IgG4, IgA1 and IgA2. In addition, the constant domains of the heavy chains of different classes and immunoglobulin are called alpha, delta, epsilon, gamma and mu, respectively.

An antibody fragment may be any part of the antibody that maintains the function of the entire antibody. Examples of antibody fragments are Fv, Fab (fragment antigen binding), Fab2 (fragments with two antigen-binding sites), all well known by a person skilled in the art. The single chain variable fragments (scFv) comprising the $V_H$ domains (the variable domain of the heavy chain) and $V_L$ (variable domain of the light chain) antibody, being these domains in a single polypeptide chain. Other formats of the antibodies of the present invention may be those known as miniantibodies or "minibodies" comprising a scFv and a constant region of CH3 type, or so-called scFv-Fc, comprising a scFv and the CH2 and CH3 constant regions. These formats increase the scFv molecular weight, avoid rapid clearance by the kidney and can be very useful for the use of a scFv in imaging technique.

The term "antigen" refers to a predetermined antigen to which the antibody is capable of binding selectively. The antigen may be a polypeptide, a carbohydrate, a nucleic acid, a lipid, a hapten or another natural or synthetic molecule. Preferably, the antigen is a polypeptide.

The inventors of the present invention have studied the affinity of the antibodies 2B1 and B11 to the ephrin B2, finding that B11 has a high affinity for the antigen, being the affinity constant ($K_D$) of 110 nM, while 2B1 has lower affinity, being the $K_D$ of 630 nM. The affinity of the binding between the recognition site and binding site of an antibody and its antigen is related to the strength of the sum total sum of noncovalent interactions between the two. The affinity of a molecule by another can be represented generally by the affinity constant, also called the dissociation constant ($K_D$). The affinity can be measured by commonly known methods such as, but not limited to the methods described herein.

When an antibody has low affinity for its antigen, is often slowly bound to it and dissociates easily. In order to improve the affinity of an antibody for its antigen, well described techniques in the literature can be employed to "mature the affinity" (Marks et al. BioTechnology 1992. 10:779:783; Barbas, C F et al. Proc. Natl. Acad. Sci. U.S.A. 1994 26; 91:3809-13). These techniques can be, among others, the "shuffling" of the $V_H$ and $V_L$ domains, or random mutagenesis.

In a preferred embodiment of the invention, the polypeptide further comprises a signal peptide. Preferably, the signal peptide is SEQ ID NO: 6, the signal peptide of the bacterial pectate lyase of *Erwinia carotovora* known as pelB. This signal peptide allows that the scFv is located in the periplasm where it folds correctly thanks to the oxidizing environment.

A signal peptide is a short sequence of amino acids between 3 and 60 which directs the transport of a polypeptide or protein to a particular subcellular location, such as the endoplasmic reticulum, mitochondria or the nucleus. The signal peptide may also direct the transport of the protein outside the cell, which could be equivalent to its secretion or its cellular transport into the periplasm, in the case of cells such as *Escherichia coli*. Some examples of signal peptide to direct secretion of a polypeptide are pelB, stli, ecotina, lamB, herpes GD, 1pp, alkaline phosphatase, invertase, alpha factor and leader sequence of protein A.

In a preferred embodiment of the invention, the polypeptide further comprises at least one marker. Preferably, the marker is selected from the list comprising: c-myc, FLAG, HA, histidine chain, GST, biotin, VSV-G, HSVtk, V5, biotin, avidin, streptavidin, maltose binding protein and a fluorescent protein. More preferably, the marker is a chain of histidines, c-myc or both. Preferably, the histidine chain comprises between 4 and 12 histidines. More preferably, the histidine chain comprising 6 histidines. In a preferred embodiment of the invention, the polypeptide comprises the markers c-myc and a chain of histidines. In a preferred embodiment of the invention, the polypeptide amino acid sequence is SEQ ID NO: 7.

The term "marker" as used in the present description refers to a marker peptide or a marker protein, which allow the identification of the protein of interest when they are produced together with this protein as a fusion protein. The marker peptide or marker protein is used for the identification and/or localization of the protein of interest because such markers correspond to binding sites to specific molecules or atoms, as the chain of histidine, GST, avidin or streptavidin, or because they are easily detectable by immunochemical techniques, such as hemaglutinin, VSV-G, HSVtk, FLAG, V5 or myc, or because they are readily observable, such as fluorescent proteins.

The marker peptide VSV-G belongs to the vesicular stomatitis virus glycoprotein. The HSVtk marker peptide belonging to the thymidine kinase of herpes simplex virus 1. The FLAG peptide is an 8 amino acid epitope specifically designed as a marker for recombinant proteins. The V5 is a small epitope present in the P and V proteins of the paramyxovirus simian virus 5 (SV5). The myc epitope has 10 amino acids and is part of the sequence of the transcription factor human c-myc.

Another embodiment of the invention is an antibody whose amino acid sequence comprises the polypeptide of the first aspect of the invention.

A second aspect of the present invention relates to a nucleic acid encoding the polypeptide of the first aspect of the invention. Preferably the nucleic acid is a vector. More preferably, the vector is an expression vector.

A nucleic acid or polynucleotide is a polymer of nucleotides of any length, including DNA and RNA. The nucleotides can be deoxyribonucleotides, ribonucleotides, modified nucleotides or any substrate that can be incorporated into a polymer by DNA or RNA polymerase or by a synthetic reaction.

The term "encodes" refers to the genetic code that determines how a nucleotide sequence is translated into a polypeptide or protein. The order of the nucleotides in a sequence determines the order of amino acids along a polypeptide or protein.

A vector is a nucleic acid molecule used to transfer genetic material to a cell. Apart from the mentioned genetic material, a vector may also contain different functional elements including elements controlling transcription, such as promoters or operators, enhancers or regions for binding of the transcription factors, and control elements for starting and ending the translation. The vectors include but are not limited to: plasmids, cosmids, viruses, bacteriophages, recombinant expression cassettes and transposons. Certain vectors are capable of replicate or divide autonomously once they are introduced into the host cell, such as bacterial vectors with bacterial replication origin or episomal mammalian vectors. Other vectors can be integrated into the host cell genome and replicated together with the cellular genome. An expression vector is one capable of directing the expression of genes to which it has been operatively linked. An expression vector is used for the transcription and translation of a gene of interest, usually controlled by a promoter. A promoter is a sequence of nucleotides that controls the transcription of the gene of interest. The promoter is operably linked to the gene of interest. "Operatively linked" refers to the functional relationship, and the location of the promoter sequence regarding the gene of interest, for example, a promoter or enhancer is operably linked to a coding sequence if it affects the transcription of the sequence. Generally, an operably linked promoter is adjacent to the sequence of interest. However, an enhancer does not need to be contiguous with the sequence of interest to control its expression.

The term "replication origin" as used in this description, refers to a nucleotide sequence where a replication fork is formed and where DNA replication initiates.

A third aspect of the invention relates to a cell comprising the vector of the second aspect of the invention. The cell may be prokaryotic, for example, but without limitation, the cell may be a bacterium such as *E. coli* which is used to produce the antibody of the invention. The cell may be eukaryotic, such as, but without limitation, yeast or insect cell, used to produce the antibody of the invention. The eukaryotic cell can be used for cell therapy, or may be a cell that has incorporated the vector of the second aspect of the invention by gene therapy. In a preferred embodiment of the invention, the cell is a mammalian cell. A mammalian cell is any cell whose species belongs to the kingdom Animalia, phylum Chordata, subphylum Vertebrata and class Mammalia.

A fourth aspect of the invention relates to a method of obtaining the polypeptide of the first aspect of the invention, comprising the steps:
(a) expressing the vector of the second aspect of the invention in a cell and (b) purifying the polypeptide expressed in step (a).

In a preferred embodiment of the fourth aspect of the invention, the cell is prokaryotic. In another preferred embodiment of the fourth aspect of the invention, the cell is eukaryotic.

A fifth aspect of the invention relates to a method for detection and/or quantification of the ephrin B2 comprising the steps:
(a) contacting an isolated biological sample with the polypeptide of the first aspect of the invention and (b) detecting and/or quantifying the complex formed by the ephrin B2 and the mentioned polypeptide in the sample used in (a).

A preferred embodiment of the fifth aspect of the invention is a method of diagnosing a disease associated with the expression of ephrin B2 comprising the steps:
(a) contacting an isolated biological sample with the polypeptide of the first aspect of the invention, (b) detecting and/or quantifying the complex formed by the ephrin B2 and the mentioned polypeptide in the sample used in (a), (c) compare ephrin B2 levels detected with control levels and (d) associating the result of the mentioned comparison to the presence or absence of disease.

A disease associated with the expression of ephrin B2 can be among others, any illness with a deregulation of angiogenesis, such as neoplastic and non-neoplastic diseases. Normeoplastic diseases which present a dysregulation of angiogenesis include but are not limited to: aberrant hypertrophy, arthritis, rheumatoid arthritis, psoriasis, sarcoidosis, atherosclerosis, diabetic retinopathy, proliferative retinopathy, neovascular glaucoma, age-related macular degeneration, diabetic macular edema, corneal neovascularization, meningioma, hemangioma, angiofibroma, thyroid hyperplasia, chronic inflammation, lung inflammation, sepsis, cerebral edema, synovial inflammation, hypertrophy of bone formation, osteoarthritis, polycystic ovary syndrome, endometriosis, Crohn's disease, ulcerative colitis, hemophilic joints, hypertrophic scar, scleroderma, trachoma, synovitis, dermatitis, preeclampsia (WO2007/127506).

An isolated biological sample is a sample isolated from a body such as the human or animal body and can come from a physiological fluid and/or any cell or tissue of an organism. The biological sample may be a tissue, for example, without limitation, a biopsy or fine needle aspiration. In a preferred embodiment, the biological sample isolated in step (a) is a biological fluid. The biological fluid may include fluids excreted or secreted from the body, as well as fluids that normally are not. The biological fluid may include, without limitation, the amniotic fluid surrounding the fetus, aqueous humor, interstitial fluid, lymph, breast milk, mucus (including nasal drainage and phlegm), saliva, sebum (skin oil), whey, sweat, tears, urine, pericardial fluid, blood and blood plasma. In a more preferred embodiment, the biological fluid is blood, blood plasma or blood serum. The biological sample isolated in step (a) of the method of the invention may be, for example, without limitation, fresh, frozen, fixed or embedded in paraffin.

The term "detect and/or quantify" the complex formed by the ephrin B2 and the polypeptide of the first aspect of the invention in an isolated biological sample, as used in the present description refers to the detection of the presence and/or the measurement of the amount or concentration, preferably in a semi-quantitative or quantitative way. The measurement can be performed directly or indirectly. Direct measurement refers to measuring the amount or concentration of the complex formed by the ephrin B2 and the polypeptide of the first aspect of the invention, based on a signal obtained directly from the mentioned complex and which is directly correlated with the number of complex molecules present in the sample. This signal, which can also be referred to as intensity signal can be obtained, for example, by measuring an intensity value of a physical or chemical property of the complex. Indirect measurement includes measurement obtained from a secondary component (eg, a different component of the complex) or a biological measurement system (for example, measuring cellular responses, ligands, "tags" or enzymatic reaction products).

The term "amount" refers to, but is not limited to the absolute or relative amount of complex formed by the ephrin B2 and the polypeptide of the first aspect of the invention and any other value or parameter associated with the complex, or that can be derived from it. Such values or parameters comprise intensity values of the signal obtained from any of the physical or chemical properties of the complex, obtained by direct measurement, for example, intensity values from mass spectroscopy or nuclear magnetic resonance. Additionally, these values or parameters include those obtained by indirect measurement.

The detection as is understood by one skilled in the art, is not intended to be correct at 100% of the analyzed samples. However, requires that a statistically significant number of samples analyzed are classified correctly. The amount that is statistically significant can be established by one skilled in the art using different statistical tools, such as, but not limited to, the determination of confidence intervals, p-value determination, Student's t test or Fisher discriminant functions. Preferably, the confidence intervals are at least 90%, at least 95%, at least 97%, at least 98% or at least 99%. Preferably the p value is less than 0.1, 0.05, 0.01, 0.005 or 0.0001. Preferably, the present invention can correctly detect the disease in at least 60%, at least 70%, at least 80%, or by at least 90% of the subjects of a given group or population analyzed.

The term "comparing" as used in the present description refers, but is not limited to comparing the amount of complex formed by the ephrin B2 and the polypeptide of the first aspect of the invention of the biological sample to be analyzed, also called biological sample problem, with an amount of complex of reference sample, which is called control. The reference sample can be analyzed, for example, concurrently or sequentially with the biological sample problem. The comparison can be performed manually or computer assisted.

A sixth aspect of the present invention relates to the use of the polypeptide of the first aspect of the invention for preparing a medicament. In a preferred embodiment of the invention, the medicament is used to inhibit angiogenesis. Preferably, for therapeutic or prophylactic treatment of a pathological condition associated with angiogenesis. More preferably, for the prophylactic or therapeutic treatment of a tumour or cancer.

A pathological condition associated with angiogenesis may be any neoplasia as well as other non-neoplastic diseases, such as, without limitation, those described in WO2007/127506.

In a preferred embodiment of the sixth aspect of the invention, the tumor or cancer is solid. Preferably, pancreatic, colon or lung cancer. A tumor or cancer is said to be solid when is a mass of tissue not containing cavities nor liquid. Depending on the cell type, solid tumours have different names, such as sarcoma, carcinoma or lymphoma.

A seventh aspect of the invention relates to a composition comprising the polypeptide of the first aspect of the invention, the nucleic acid or vector of the second aspect of the invention, or the cell of the third aspect of the invention. In a preferred embodiment of the seventh aspect of the invention, the composition is a pharmaceutical composition. Preferably, it is also characterized by comprising a pharmaceutically acceptable excipient. Furthermore, the excipient must be pharmacologically acceptable.

An "excipient" is a component of a pharmaceutical composition that is not an active compound but a diluent, a carrier or a filling, among others, which is considered "pharmaceutically acceptable" when it is safe, non-toxic and has no adverse effects. The term "excipient" refers to a substance that helps in the absorption of the compound, stabilizes it or helps in the preparation of the medication in the sense of giving consistency or providing flavors that make it more pleasant. Thus, the excipients may have the function of keeping together the ingredients such as starches, sugars or celluloses, sweeten function, dye function, drug protection function such as to isolate the air and/or moisture, filling function of a tablet, capsule or other form of presentation such as dibasic calcium phosphate, disintegrating function to facilitate dissolution of the components and their absorption in the intestine, without excluding other types of carriers not listed in this paragraph.

The excipient term "pharmaceutically acceptable" means that the carrier is permitted and evaluated so as not to cause damage to the organisms to which it is administered. Moreover, the carrier must be pharmaceutically suitable, it must allow the activity of the compounds of the pharmaceutical composition, i.e., must be compatible with those components.

The "vehicle" or carrier is preferably an inert substance. The vehicle function is to facilitate the incorporation of other compounds, allow a better dosage and administration or give consistency and form to the pharmaceutical composition. Therefore, the carrier is a substance that is used in the medicine to dilute any component of the pharmaceutical composition of the present invention to a given volume or weight, or even with non-diluted components can allow better dosage and administration or give consistency and shape to the medicine. When the presentation is liquid, the pharmaceutically acceptable carrier is the diluent.

In another even more preferred embodiment, the pharmaceutical composition further comprises another active substance. Besides the requirement of therapeutic efficacy, which may necessitate the use of other therapeutic agents, there may be additional rationales which compel or greatly recommend the use of a combination of a compound of the invention and another therapeutic agent. The term "active" means any material, regardless of human, animal, vegetable, chemical or otherwise origin with an appropriate activity to be a drug.

In a preferred embodiment of the seventh aspect of the invention, the pharmaceutical composition further comprises an angiogenic agent. An antiangiogenic agent is a molecule capable of inhibiting angiogenesis, vasculogenesis, or undesirable vascular permeability, either directly or indirectly. Examples of antiangiogenic agents are those molecules capable of blocking one angiogenic agent, such as for example antibodies against VEGF, VEGF receptor or small molecules that block VEGF pathway, all well described and known.

In a preferred embodiment of the seventh aspect of the invention, the pharmaceutical composition further comprises a chemotherapeutic agent. A chemotherapeutic agent is a compound useful in the treatment of cancer. Examples of chemotherapeutic drugs are cytotoxic compounds as antraciclines, daunorubicin, adriamycin, derivatives of docetaxel, vinca alkaloids, vincristine, carmustine, cisplatin, fluorouracils, cytostatic compounds such as polyamine inhibitors, tamoxifen or prodasone sandostatin, or compounds that induce apoptosis as sodium butyrate or mitomycin C, antibiotics such as penicillins, betalactamins, cephalosporins, cyclins, aminoglycosides, macrolides, or sulfonamides, or antivirals like AZT, protease inhibitors or acyclovir, retrovir or foscarnet.

An eighth aspect of the invention relates to use of the composition of the seventh aspect of the invention for preparing a medicament. In a preferred embodiment of this aspect of the invention, the medicament is used to inhibit angiogenesis. Preferably, for therapeutic or prophylactic treatment of a pathological condition associated with angiogenesis. More preferably, for the prophylactic or therapeutic treatment of a tumour or cancer. In a preferred embodiment, the tumour or cancer is solid. Preferably, the cancer is pancreatic, colon or lung.

In a preferred embodiment of the eighth aspect of the invention, a therapeutically effective amount is administered. The term "therapeutically effective amount" refers to an amount that, administered in a dose and during the period of time necessary, is effective in achieves the desired prophylactic or therapeutic result. A "therapeutically effective amount" of the polypeptide or pharmaceutical composition of the invention may vary with the stage of disease, age, sex and weight of the individual, and refers to an amount which has no toxicity or side effects and is capable to achieve the desired prophylactic or therapeutic effect. An "individual" is a vertebrate. Preferably, the vertebrate is a mammal. More preferably, the mammal is a human. Among mammals are include, but without limitation, farm animals (such as cows), animals involved in sports, pets (such as cats, dogs and horses), primates, mice and rats.

In each case the format of the drug is adapted to the type of administration used, therefore, the composition of the present invention can be presented under the form of solutions or any other form of clinically permissible administration and in a therapeutically effective amount. The pharmaceutical composition of the invention may be formulated in solid, semisolid, liquid or gaseous, such as tablet, capsule, powder, granule, ointment, solution, suppository, injection, inhalant, gel, microsphere or aerosol. According to a further preferred embodiment of the present invention, the pharmaceutical composition is in a form adapted to oral or parenteral administration.

The form adapted to oral administration refers to a physical state which would permit the oral administration. Such form adapted for oral administration is selected from the list comprising, but not limited, drops, syrup, tea, elixir, suspension, extemporaneous suspension, drinkable vial, tablet, capsule, granule, cachet, pill, tablet, lozenge, troche or lyophilized.

The form adapted for parenteral administration refers to a physical state which would permit the injection administration, preferably in liquid state. Parenteral administration can be carried out via intramuscular, intraarterial, intravenous, intradermal, subcutaneous or intraosseous but not limited solely to these types of parenteral administration routes.

Another possibility is that the pharmaceutical composition is present in a form adapted for sublingual administration, nasal, intrathecal, bronchial, lymphatic, rectal, transdermal or inhalation.

Throughout the description and claims the word "comprise" and its variants do not intend to exclude other technical features, additives, components or steps. For those skilled in the art, other objects, advantages and features of the invention will emerge partly from the description and partly from practice of the invention. The following examples are provided by way of illustration and are not intended to be limiting of the present invention.

Apoptotic cells were detected by staining for active caspase 3, the proliferative activity was analyzed by Ki67 staining, vascularity was labeled by CD34 staining and the lymphatics vessels were detected by staining LYVE1. Subsequently cells were counted or the positive areas and mean values were plotted for all fields counted together with their respective standard deviations. *=p<0.0001**=<0.001.

Figure 11A:
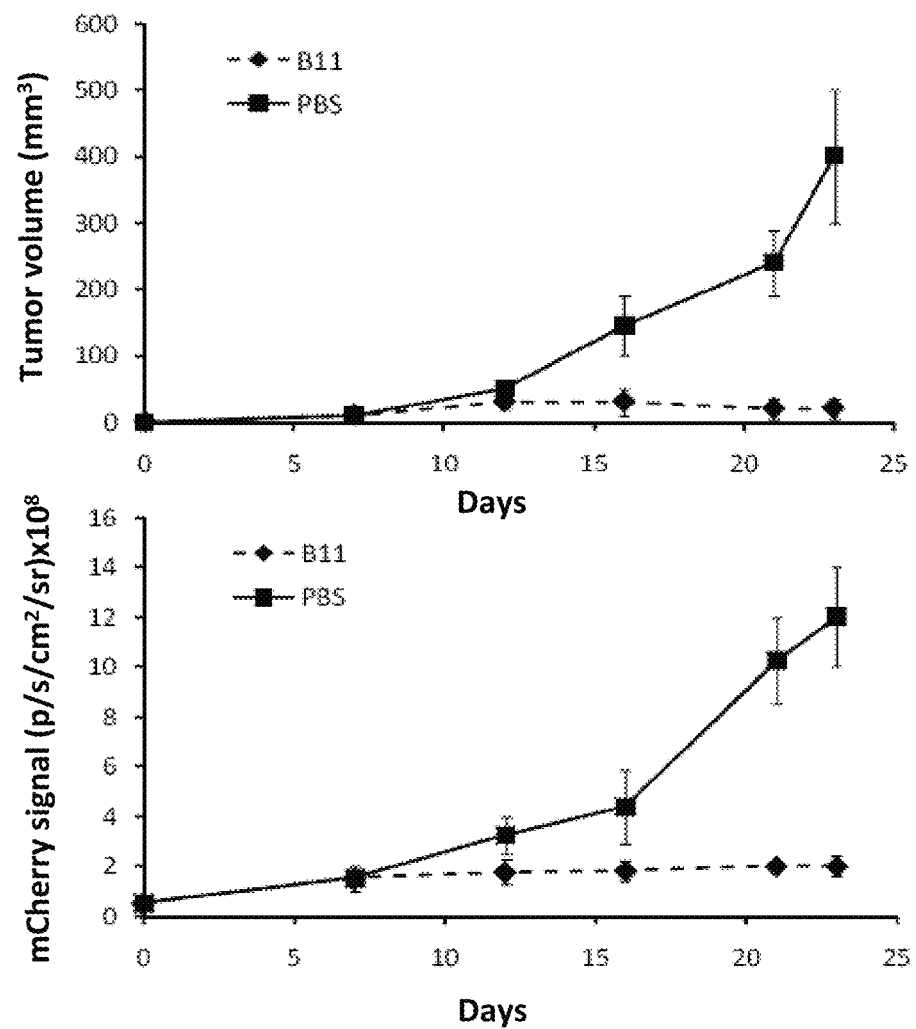

FIG. 11. B11 is Able to Inhibit Tumour Growth in Mice Xenografted with colon carcinoma cells (SW620) (A) and lung carcinoma cells (H460) (B). The graphs show the mean tumour volumes (upper panels) and the mean fluorescence intensities (lower panels) with standard deviation at each point in the groups treated with 20 mg/kg of B11 and control groups treated.

Figure 12A:
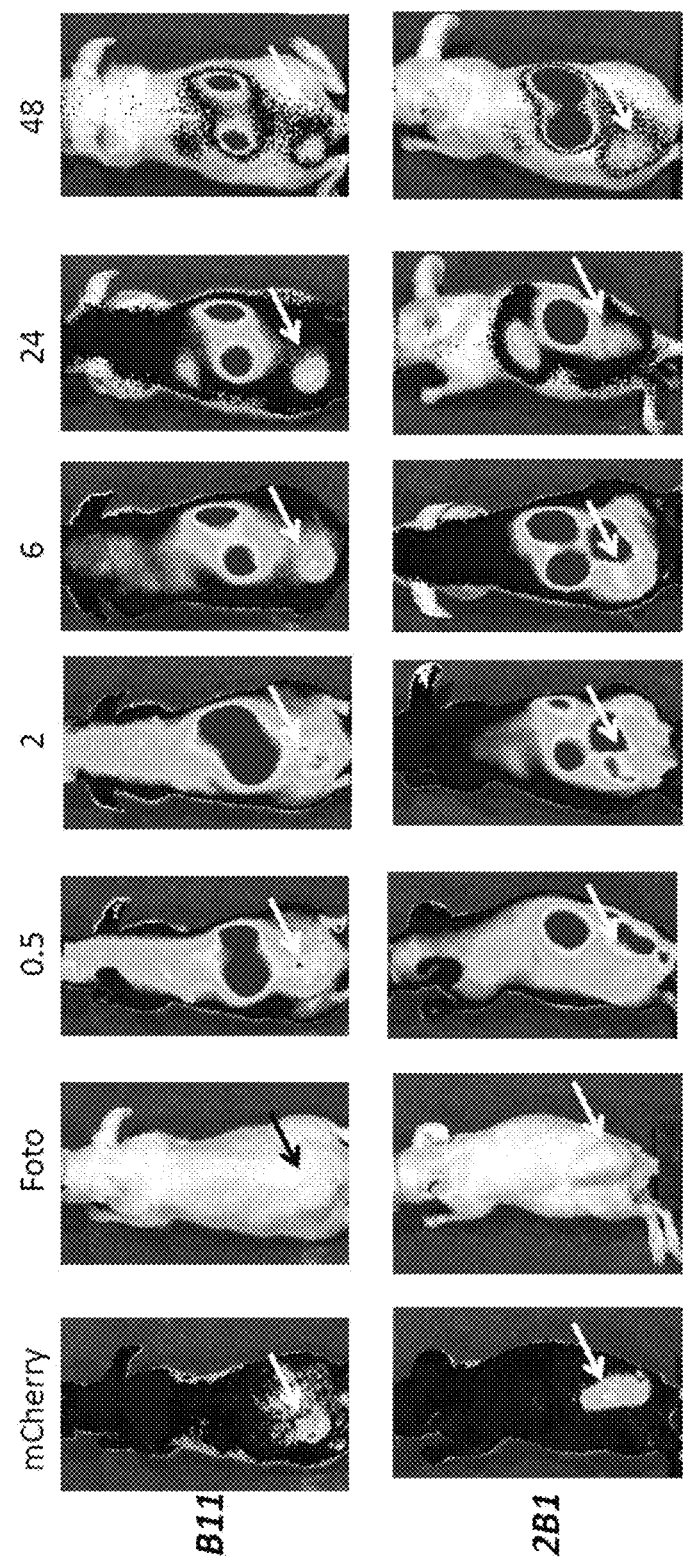

FIG. 12. Biodistribution Analysis of B11 and 2B1 and Location of Tumor Masses. Athymic nu/nu mice were xenografted with H460 cells of lung carcinoma stably expressing the fluorescent protein mCherry. When the tumour reached a size detectable macroscopically and with fluorescence intensity at 610 nm, the appropriate fluorochrome-conjugated scFv AlexaFluor® 750 were administered intravenously. A. Images dorsal regions at 0.5, 2, 6, 24 and 48 hours after administration of the scFv. The localization of tumours is indicated with an arrow. B. Fluorescence intensity at 750 nm of the tumours excised at 6 and 48 hours after administration of the scFv B11 and 2B1 labelled with AlexaFluor® 750 and the negative control (C−) treated with PBS.

EXAMPLES

Below the invention will be illustrated by means of tests made by the inventors, which demonstrates antibody specificity against ephrin B2 of the invention as well as their effectiveness in inhibiting the formation of new blood and lymphatic vessels.

Example 1

Identification and Characterization of Novel Human Antibodies Against Ephrin B2

Figure 1:
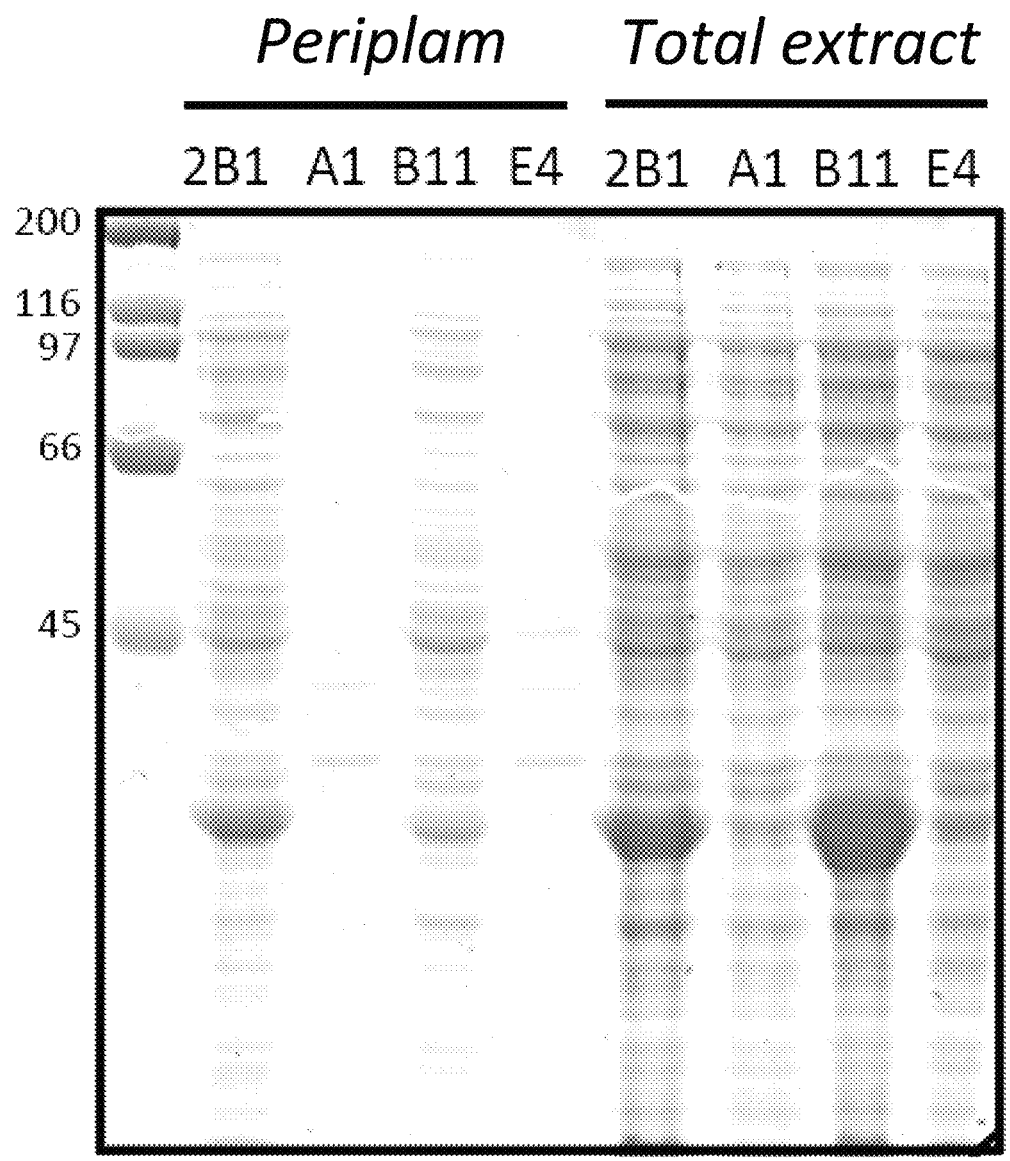
FIG. 1. Expression of the Selected Clones in *E. Coli*. Analysis by acrylamide gel electrophoresis (SDS-PAGE) and Coomassie blue staining of the scFvs expression selected against ephrin B2 (2B1 clones, A1, B11 and E4) in *E. coli* (total extract) and of the corresponding periplasmic fraction isolated by mild osmotic shock (periplasm). The molecular weights are indicated to the left of the figure in kDa.
Figure 2:
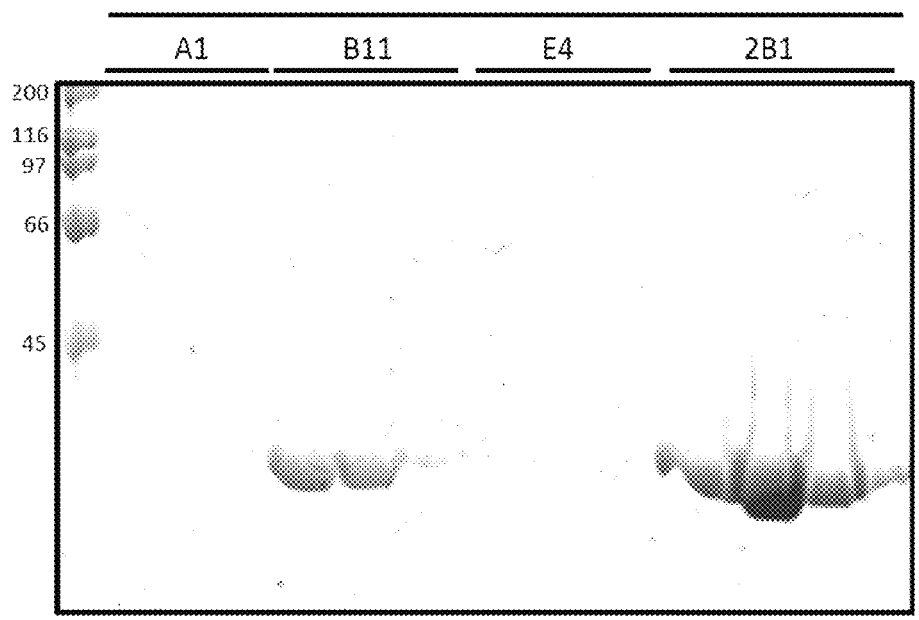
FIG. 2. Clones 2B1 and B11 are Purified in Larger Quantities. Analysis of purifications of scFvs A1, B11, E4 and 2B1 specifics of ephrin B2 by acrylamide gel electrophoresis (SDS-PAGE) and Coomassie blue staining. The scFvs present in the respective periplasmic extracts were purified by affinity chromatography on immobilized $Ni^{2+}$. The figure shows the different fractions of elution chromatography of each scFv. The molecular weights are indicated in kDa.

From a library of human antibodies expressed on the surface of phage M13 and through successive rounds of selection against the extracellular region of the ephrin B2, expressed in mammalian cells and purified by affinity chromatography, was obtained a collection of phage clones that reacted positively with ephrin B2 antigen by ELISA. These clones were sequenced with specific primers and were identified 4 single chain variable fragments (scFv) of mutually different sequences in both $V_H$ (variable heavy chain) and $V_L$ (variable light chain), called A1, B11, E4 and 2B1. Subsequently, it was performed the analysis of the expression and purification of each of the selected scFv. To do this they were subcloned into vector pET28b under the promoter of the T7 RNA polymerase in order to provide the fragments with a histidine tail to facilitate its purification by affinity chromatography. Recombinant vectors were generated and transformed into the strain of *E. coli* BL21 (DE3) to subsequently induce its expression with IPTG. Periplasmic fraction was prepared by mild osmotic shock and tested for the presence of the scFv by SDS-PAGE (FIG. 1). Then, it was proceeded to the purification of scFv present in periplasmic fractions using nickel affinity chromatography followed by a buffer exchange to PBS by gel filtration (FIG. 2). The highest yield was obtained in the case of clone 2B1 (whose sequence is SEQ ID NO: 8), followed by clone B11 (whose sequence is SEQ ID NO: 7). However, the expression of the scFv A1 and E4 were so low, that the amounts reached were insufficient to obtain further characterization of these antibodies (FIG. 2). Therefore, B11 and 2B1 clones were finally selected to analyze its reactivity. Functional assays, by ELISA showed that the antibodies were expressed in a functionally active form to specifically recognize their target antigen, the ephrin B2.

Figure 3:
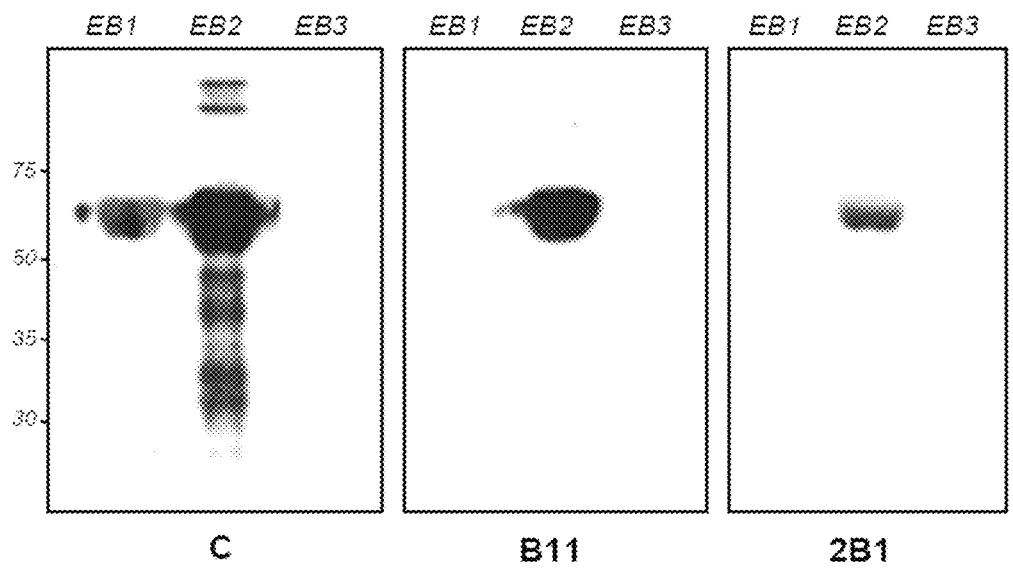
FIG. 3. Clones B11 and 2B1 are More Specifics. Determination of the specificity of the scFv anti-ephrin B2 selected against different ephrin B by immunoblot. Commercial Recombinant proteins ephrin B1-Fc (EB1) mouse, ephrin B2-Fc (EB2) of mouse and ephrin B3-Fc (EB3) human were electrophoretically separated and transferred to nitrocellulose membranes. Subsequently, the reactivity of B11 and 2B1 clones together with a commercial antibody anti-ephrin B2 as a control (C) was analyzed. The molecular weights are indicated to the left of the figure in kDa.

The specificity of the two antibodies was confirmed by immunoblotting (Western blot) and ELISA analysis of the reactivity of B11 and 2B1 with other components of the ephrins B family: the ephrin B1 and ephrin B3, in commercial recombinant forms, in comparison with reactivity with ephrin B2 (FIG. 3). As control, we used an anti-ephrin B2 Commercial (R & D). Both antibodies, B11 and 2B1, only recognized the ephrin B2, demonstrating its high specificity for this protein, even more than the commercial antibody that also recognizes the ephrins B1 and B3. These results were confirmed by ELISA.

Selection of Single Chain Variable Fragments (scFv) from Specific Ephrin B2 Antibodies from Phage Libraries It was used the protein display technology on the surface of phage (Phage display) with a library of human antibodies from individuals non-immunized of $1.5 \times 10^{10}$ scFv. The first round of panning was performed with the extracellular region of the ephrin B2 fused to the Fc domain of human IgG, expressed and purified from mammalian cells as antigen immobilized on ELISA plates (Enzyme-linked immunosorbent assay, Maxisorp, Nunc) at 1 µg/well for 16 hours at 4° C. in PBS (phosphate buffer saline). After 3 PBS washes of wells, it was carried out a step of blocking with 2% milk in PBS for 2 hours at 37° C., followed by incubation of the library during 2 hours at 37° C. Phages bound unspecifically were removed by successive washing with PBS-0,1% Tween, while antigen-specific phages were eluted with 100 µl of trypsin. Cells were infected with *Escherichia coli* strain TG1 (MRC Geneservices) in exponential growth (optical density at a wavelength of 600 nm ($OD_{600}$) of 0.4) for 30 minutes at 37° C. with the eluted phage. Infected bacteria were plated on TYE plates (TYE, Tryptone Yeast Extract) supplemented with 100 µg/ml ampicillin and 1% glucose (v/v) and grown for 16 hours at 37° C. Next, the bacteria were collected from the plates with 2×TY medium (16 g/l tryptone, 10 g/l yeast extract and 5 g/l NaCl) supplemented with 15% glycerol and 50 µl of the diluted bacteria were collected in 50 ml of 2×TY medium supplemented with 100 µg/ml ampicillin and 1% glucose, cultures were incubated until reaching the exponential phase and the cells were infected with $2.5 \times 10^{11}$ helper phage KM13 (MRC Geneservices). After 30 minutes of incubation at 37° C., the cultures were centrifuged, the pellets were resuspended in the same volume of 2×TY medium supplemented with 100 µg/ml ampicillin, 50 µg/ml kanamycin and 0.1% glucose and grown overnight at 30° C.

The phage from each round of selection was precipitated from the culture medium. For this the cultures were centrifuged at 3,300×g for 15 minutes and was added 10 ml of polyethylene glycol (PEG)/NaCl and 40 ml of supernatant were left 1 hour on ice. Then, they were centrifuged at 3,300×g for 30 minutes and the supernatants were discarded. The precipitates were resuspended in 2 ml of PBS and were centrifuged at 11,600×g for 10 minutes. The supernatants were recovered and the phages were used for the next round of selection, similar to that described above, with the particularity that decreasing amounts of antigen were used to improve the affinity of the antibodies. Bound phages in the second round were amplified and re-submitted to a third round of selection to get an enrichment of those carrying a reactive scFv against ephrin B2.

ELISA for Phages

ELISAs for phages were performed to assess the degree of enrichment of specific phages of ephrin B2, resulting from each round of selection. Flexible ELISA plates (Falcon, B D Biosciences) were coated with 0.3 μg of ephrin-B2-Fc and an irrelevant protein as a negative control in PBS at 4° C. for 16 hours. After several washes with PBS, the plates were blocked with 2% milk in PBS for 2 hours at room temperature, followed by incubation with different dilutions of phage from each round of selection in PBS-2% milk for 1 hour at room temperature. Wells were washed again with PBS-Tween 20 at 0.1% and were incubated with a 1:5000 dilution of a monoclonal anti-M13 antibody conjugated to peroxidase (HRP) (GE Healthcare) for 1 hour at room temperature. After four washes with PBS-Tween 20 at 0.1%, it was developed with TMB (3,3', 5,5'-tetramethylbenzidine) (Sigma). The colorimetric reaction was stopped with 1M sulfuric acid and absorbance was measured at 450 nm.

Figure 4:
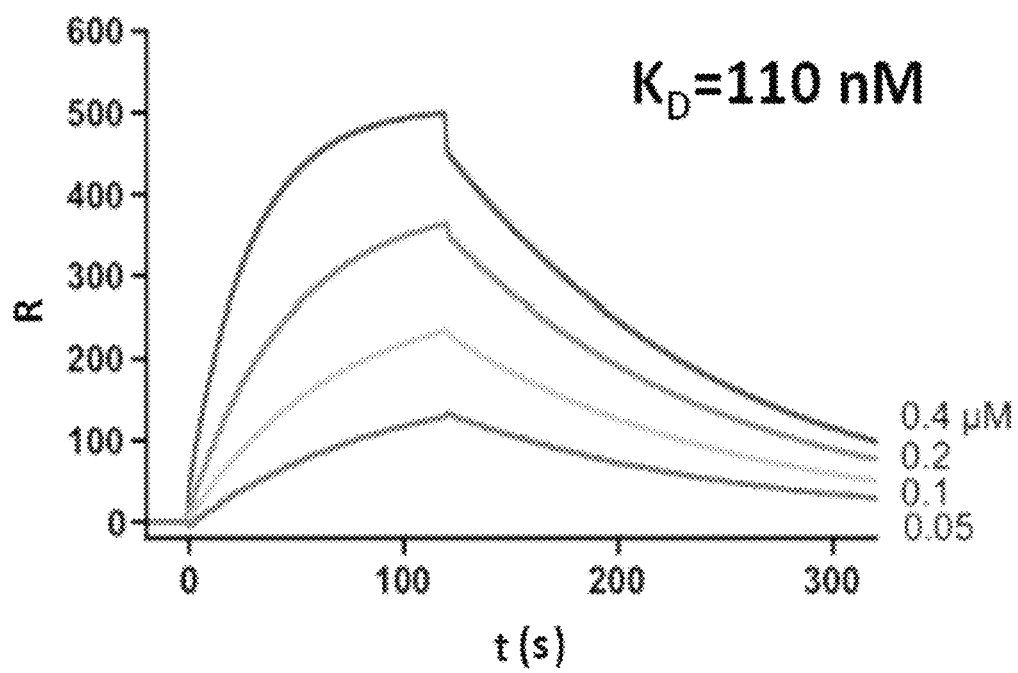
FIG. 4. Analysis of the Affinity of scFv Anti-Ephrin B2 by Biacore™. The sensorgrams represent the response against time (s) corresponding to the binding curves of clone B11 (A) to ephrin B2 immobilized using four different concentrations (0.4, 0.2, 0.1, 0.05 µM) and clone 2B1 (B) at concentrations of 30, 20, 10 and 7.5 µM, from which the respective affinity constants ($K_D$) were calculated, being $K_D$ of 110 nM for clone B11 and 630 nM for clone 2B1.
Figure 4:
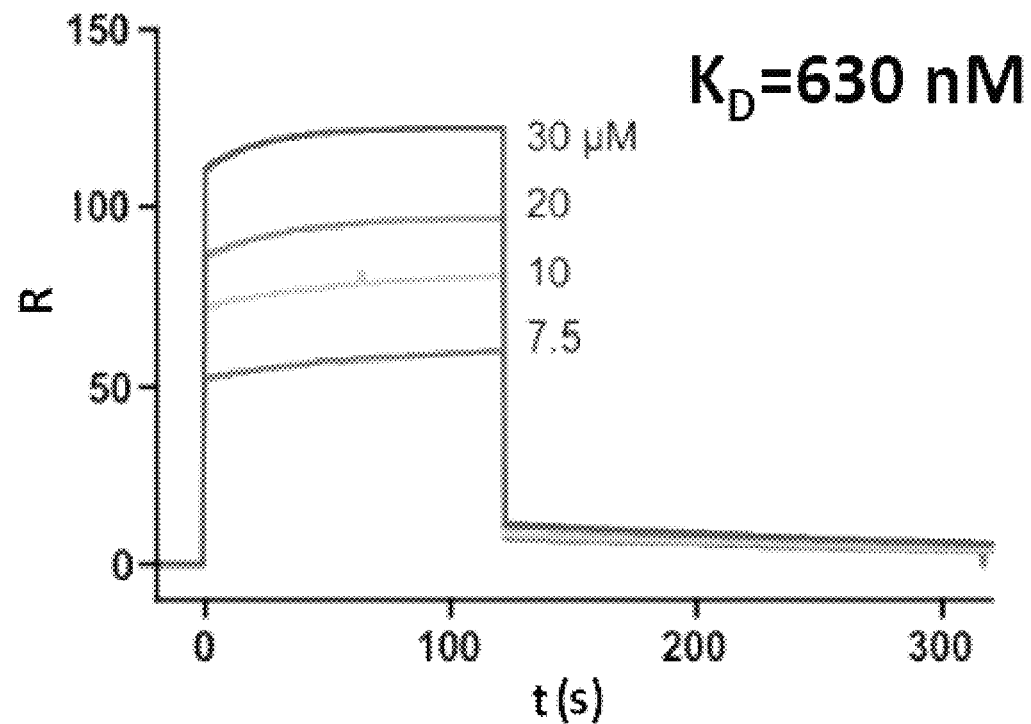
Figure 5:
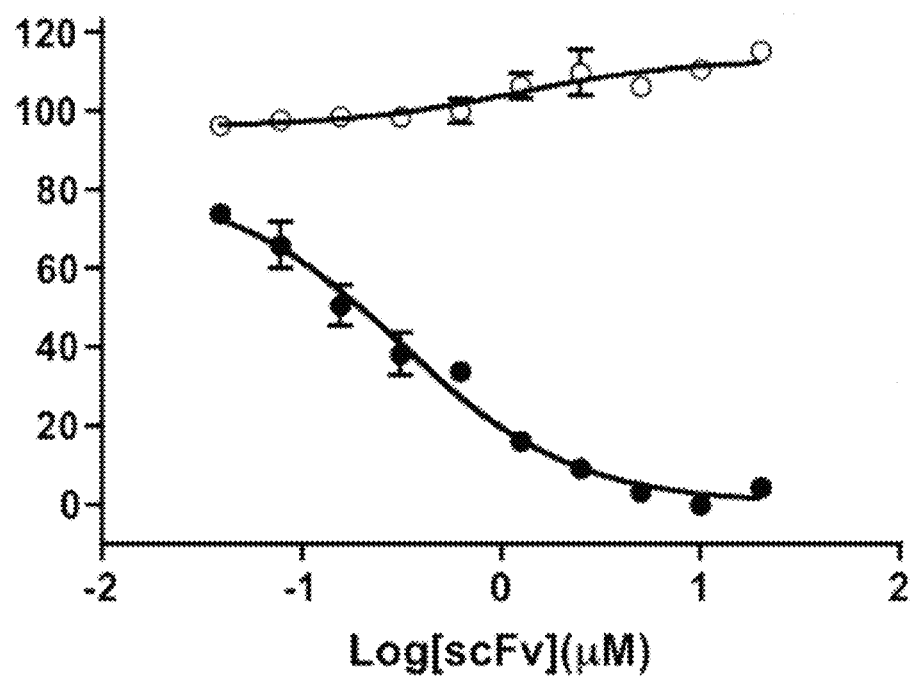
FIG. 5. Study Blocking the Binding of Ephrin B2 to Eph B4. A. Graph showing the percent of binding of ephrin B2 to Eph B4. Binding inhibition tests of ephrin B2 to Eph B4 in the presence of scFv anti-ephrin B2 by surface plasmon resonance. Serial dilutions of scFv B11 (•) or 2B1 (○) were mixed with ephrin B2 and injected over Eph B4 immobilized on a chip. The relative amount of ephrin B2 bound to Eph B4 was measured immediately after injection of each sample and plotted as a function of the concentration of scFv. The figure shows the average values for each concentration of scFv with error bars indicating the standard deviation (n=3). B. The scFv B11 is capable of blocking the interaction between ephrin B2 and Eph B4 receptor in a cellular assay. Analysis of tyrosines phosphorylation of the Eph B4 receptor in HUVEC cells in response to stimulation with ephrin B2 overexpressed on the surface of HEK293 cells. HUVEC and HEK293 cells overexpressing ephrin B2 were cocultured for 20 minutes in the presence or absence of anti-ephrin B2 scFv. After Eph B4 receptor immunoprecipitation, it was analyzed the total amount of this protein (lower panel) and its level of phosphorylation (upper panel) by immunoblot.
Figure 5:
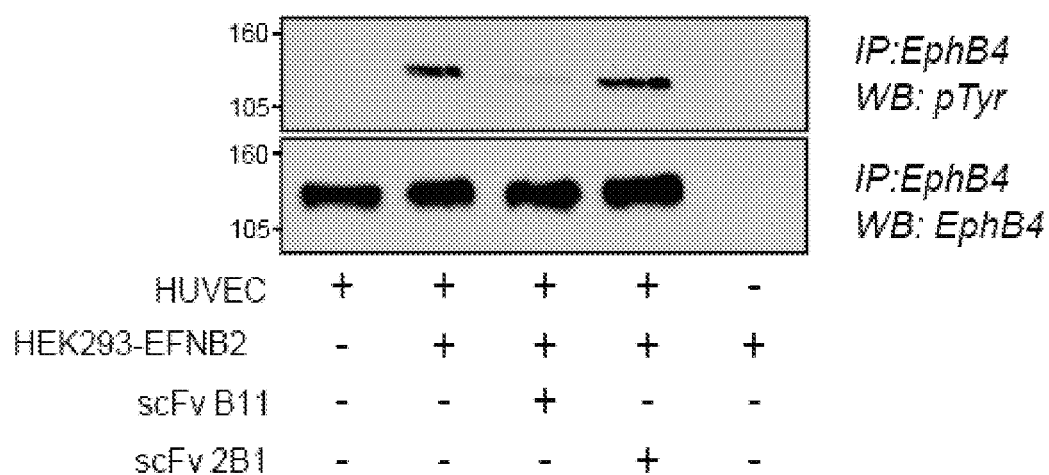

The two selected scFv, B11 and 2B1, were characterized using various techniques. First we determined the antibodies affinity constants to the ephrin B2 by means of surface plasmon resonance technique on a Biacore X, with the extracellular region of the immobilized ephrin B2 and different dilutions of purified scFv. B11 clone showed the highest affinity constant, this being of 110 nM, whereas the affinity of clone 2B1 was lower, 630 mM (FIG. 4). Then, it was analyzed, using the same technique, the capacity of the antibodies to compete for the binding of ephrin B2 to its natural receptor Eph B4. To this end, Eph B4-Fc was immobilized on a chip and the binding to ephrin B2 was measured in the presence of different concentrations of B11 or 2B1. The presence of B11 prevents ephrin B2 to Eph B4 binding in a concentration dependent manner with an $IC_{50}$ of 0.3 μM (FIG. 5), indicating that B11 competes for the same binding site of the Eph B4 receptor. However, the 2B1 antibody has no blocking effect (FIG. 5).

ELISA of Monoclonal Phages

Individual colonies were picked from the third round of selection and were grown overnight at 37° C. under stirring in 100 μl of 2×TY medium supplemented with 100 μg/ml ampicillin and 1% glucose in 96-well plates (Sarstedt). The next day the cultures were diluted 100-fold in the same medium and were incubated for 2 hours at 37° C. under stirring. Next, it was added 25 μl of medium with $10^9$ KM13 helper phages and were incubated for 1 hour at 37° C. Bacteria were centrifuged and the cell pellet was resuspended in 2×TY supplemented with 50 μg/ml kanamycin and grown overnight at 30° C. Finally, the cultures were centrifuged and 50 μl of the supernatant was used for the ELISA in the same conditions described above.

Sequence Analysis

Coding sequences from scFv positive were amplified by PCR using the oligonucleotides or pelBForward primers (SEQ ID NO: 2) 5'-CATAATGAAATACCTATTGCCTA-3' and cmycReverse (SEQ ID NO: 3) 5'-CTTATT-AGCGTTTGCCATT-3'. PCR products were treated with enzymes ExoI (USB) to remove the oligonucleotides non used, and SAP (USB) to remove dNTPs left over at 37° C. for 30 minutes and at 80° C. for 15 minutes, and such products were sequenced with both oligonucleotides. Once obtained the sequences, these were compared with each other to determine the number of unique sequence clones using the ClustalW program and the translation tool ExPASy Proteomics Server.

Subcloning of scFv into pET28b

To provide to the selected scFv a histidine tail which facilitates its purification, these were cloned into the vector pET28b (Novagen). ScFvs were amplified by PCR using primers pET28-scFvMehta 5' (SEQ ID NO: 4) 5'CAGTCAT-CATGAAATACCTATTGCCTAC3' and pET28-scFvMehta3' (SEQ ID NO: 5) 5'CACCGGACTCGAGTGCGGC-CCCATTCAG3' including two restriction sites XhoI and RcaI, respectively, for subsequent cloning into the pET28b vector, previously digested with NcoI, site compatible with RcaI and XhoI. The ligation of digested insert and vector was performed by overnight incubation at 16° C. with T4 ligase enzyme (Roche) placing an insert:vector molar ratio of 3:1. *E. coli* strain DH5a library competent cells (Invitrogen) were transformed by heat shock and were selected on plates of LB-Agar (LB, "lysogeny Broth") with 50 μg/ml kanamycin. A positive colony of each construction was inoculated in LB supplemented with kanamycin and was cultured at 37° C. overnight. The recombinant vectors were purified using the Wizard kit (Promega) and sequence was verified by DNA sequencing.

Expression and Purification of scFv

*E. coli* strain BL21 (DE3) competent cells were transformed with pET28 recombinant plasmids by heat shock. Transformant bacteria were selected on LB plates with 50 μg/ml kanamycin. It was conducted scFv expression by induction with IPTG (isopropyl-β-D-1-thiogalactopyranoside) to a final concentration of 1 mM when the $OD_{600}$ of the cultures was 0.6. We analyzed the levels of scFv expression by SDS-polyacrylamide gels (sodium dodecyl sulfate), followed by staining with Coomassie brilliant blue. Since the functional scFv is concentrated in cell periplasmic region, it was effected lysis of the bacterial outer wall by mild osmotic shock, cells were resuspending in 1/50 volume of TES buffer (200 mM Tris-HCl pH 8.0, 0.5 mM EDTA, 0.5 M sucrose) supplemented with 20 μg/ml benzamidine (Sigma) and 10 μg/ml soybean trypsin inhibitor (Sigma) and subsequently diluting 1.5 times in 0.2×TES buffer. The lysates were left for 30 minutes on ice, centrifuged at 16,250×g for 10 minutes and supernatants were collected containing the periplasmic fraction.

Purification of scFv was performed by affinity chromatography on immobilized metal (IMAC) using columns of $Ni^{2+}$ HisTrap (GE Healthcare) followed by desalting on a column of gel filtration HiPrep 26/10 Desalting (GE Healthcare) coupled in tandem on a computer ÄKTAxpress. As equilibration buffer of the affinity column was used 20 mM sodium phosphate pH 7.4, 0.5 M NaCl, 20 mM imidazole, and as the elution buffer, the same as balancing with a concentration of imidazole of 0.3 M. This buffer was exchanged for PBS by gel filtration.

Immunoblot (Western Blot)

Recombinant mouse proteins ephrin B1-Fc, mouse ephrin B2-Fc and human ephrin B3-Fc (R & D) were separated electrophoretically in polyacrylamide-SDS 10% gels and transferred onto nitrocellulose membrane (GE Healthcare). After blocking the membrane with PBS-3% skimmed milk powder for 1 hour, it was incubated with 1:5 diluted periplasmic fraction in PBS-3% powdered milk for 16 hours at 4° C. The secondary antibodies used were anti c-Myc (Sigma) at a 1:1000 dilution for 2 hours at room temperature and anti-mouse peroxidase conjugate (Sigma) diluted 1:5000 for 1 hour at room temperature. Visualization was performed by incubation with ECL reagent (ECL, "Enhanced Chemiluminescence") (GE Healthcare).

Analysis of the Kinetic Constants of scFv

To study the affinity constants of the scFv was used the technique of surface plasmon resonance with the BIAcore X equipment (BIAcore). The ephrin B2-Fc was covalently bound to CM5 chip surface (GE Healthcare) upon activation of the carboxyl groups of the dextran matrix of the chip with 0.4 M EDC (1-ethyl-3-(-dimethylaminopropyl)-carbodiimide) and 0.1 M NHS(N-hydroxysuccinimide) in a 1:1 ratio for 7 minutes at a flow rate of 10 μl/minute. The ephrin B2-Fc protein was diluted to 10 μg/ml in 10 mM sodium acetate at pH 4 and 30 μl of this solution was passed over the chip surface at a flow rate of 10 μl/min in HBS-EP buffer (10 mM HEPES pH 7.4, 150 mM NaCl, 3 mM EDTA, 0.005% surfactant P20) (GE Healthcare). The excess activated ester groups were blocked by injection of 1M ethanolamine pH 8.5 at a flow rate of 10 μl/minute for 7 minutes. Using this protocol, approximately 2,000 response units (RU) of ephrin B2 were immobilized.

To determine the affinity constants of scFv, different dilutions of antibodies in increasing order were injected sequentially, at a flow rate of 30 μl/minute. After obtaining the sensorgrams, the affinity constants were calculated using the evaluation program BIAsoftware by Langmuir 1:1 model.

Analysis of Competition for Binding to Eph B4

The ability of scFv to inhibit the binding of ephrin B2 to its EphB4 receptor was analyzed by surface plasmon resonance competitive binding assay. Soluble Eph B4 (R&D) was conjugated to a CM5 chip (GE Healthcare) using the same protocol described above. Serial dilutions of each scFv were mixed with a constant concentration (0.2 μM) of ephrin B2-Fc in HBS-EP buffer and 30 μl of each mixture was injected at a flow of 20 μl/minute onto the coated chip of Eph B4. The relative amount of ephrin B2 bound to Eph B4 is represented as a function of the corresponding concentration of antibody.

Blockage of EphB4 Signaling with the scFv B11 Anti-Ephrin B2

To test the ability of the anti-ephrin B2 scFv to block activation of Eph B4 through ephrin B2-induced phosphorylation, it was performed a cellular assay in which HEK293 cells transiently overexpress ephrin B2 were used to stimulate HUVEC cells characterized by expressing high level of Eph B4 but low levels of ephrin B2. The result is shown in FIG. 5 B. The ephrin B2 expressed on the surface of HEK293 cells induces an efficient phosphorylation of Eph B4 in HUVEC cells, after incubation of the two cell types for 20 minutes. However, the presence of scFv B11 in this process resulted in almost complete inhibition of the phosphorylation of Eph B4, indicating that treatment with scFv B11 blocks the interaction between the ephrin B2 and its receptor Eph B4 in the context of direct contact between cells. This effect was not observed when performing the treatment with the scFv 2B1. In the case of scFv 2B1, Eph B4 phosphorylation levels were similar to those observed in the absence of antibodies.

Phosphorylation Cellular Assay of Eph B4

HEK-293 cells grown in RPM1 (Sigma) supplemented with 5% fetal bovine serum were transfected with plasmid pcDNA3-ephrin B2. HEK-293 cells were seeded at $4.5 \times 10^6$ in a plastic bottle T-75 (Nunc). The next day, a mixture was prepared with 20 βg of pcDNA3-ephrinB2 and 60 μl of FUGENE transfection reagent (Roche) in 1 ml of OPTIMEM medium (Invitrogen) and it was incubated 30 minutes at room temperature. The cell monolayer was washed several times with OPTIMEM medium (Invitrogen) without serum and it was added the DNA-FUGENE mixture. After incubation for 5 hours at 37° C. and 5% $CO_2$, the medium was removed and RPM1 was added containing 5% fetal bovine serum. At 48 hours, the transfected cells were raised with PBS-5 mM EDTA and $5 \times 10^6$ cells were added to a P100 plate (Falcon) with HUVEC cells grown to confluence in EGM Bullet Kit medium (Lonza), supplemented with 10% fetal bovine serum in the presence or absence of 20 μg/ml of scFv anti-ephrin B2.

After incubation for 20 minutes at 37° C. and 5% $CO_2$, the cells were lysed with lysis buffer (100 mM Tris HCl pH 8.0, 150 mM NaCl, 1 mM EDTA, 5 mM DTT, 0.5% Triton X100) supplemented with protease inhibitor cocktail (Roche) and phosphatase (Sigma). The lysate was centrifuged 25 minutes at 16.000×g at 4° C. and then the supernatant was incubated for 2 hours at 4° C. with a preformed complex over 16 hours at 4° C. with a specific antibody against Eph B4 (R&D) and G protein-coupled to Sepharose (GE Healthcare). Finally, the immunocomplex was washed twice with lysis buffer and electrophoresed on 7.5% polyacrylamide gel SDS-PAGE.

Detection of phosphorylated Eph B4 was performed by immunoblot. To do this, proteins immunoprecipitated by anti-Eph B4 and separated by electrophoresis were transferred to a nitrocellulose membrane Hybond-C (GE Healthcare) and blocked with PBS supplemented with Tween-20 (Sigma) at 0.05% and Phosphoblocker® blocking agent (Cell Biolabs, Inc.) at 3% for 1 hour at room temperature. Then, the membrane was incubated with monoclonal antibody 4G10 anti-phosphotyrosine conjugated to peroxidase (Millipore) diluted at 1:2000 for 16 hours at 4° C. Visualization was performed using chemiluminescent detection by SuperSignal® West Femto Substrate (Thermo Scientific). For detection of total Eph B4, the same membrane was regenerated with Strong Plus ReBlot agent (Chemicon) for 15 minutes at room temperature and incubated with anti-Eph B4 antibody (R&D) diluted at 1:1000 in PBS with 0.05% Tween-20 and 5% skimmed milk for 16 hours at 4° C. After several washes with PBS with 0.05% Tween-20, the membrane was incubated with peroxidase conjugated anti-goat antibody (1:5000) (Dako) for 2 hours at room temperature and the bands were visualized with ECL Plus reagent (GE Healthcare).

Example 2

Antiangiogenic Activity of B11 and 2B1 Antibodies in HUVEC Cells In vitro

The effect of B11 and 2B1 antibodies on angiogenic capacity and endothelial cell migration were analyzed. For this, experiments of tube formation in Matrigel and in vitro wound healing assays with HUVEC cells (Human Umbilical Vein Endothelial Cells) were conducted respectively.

Figure 6:
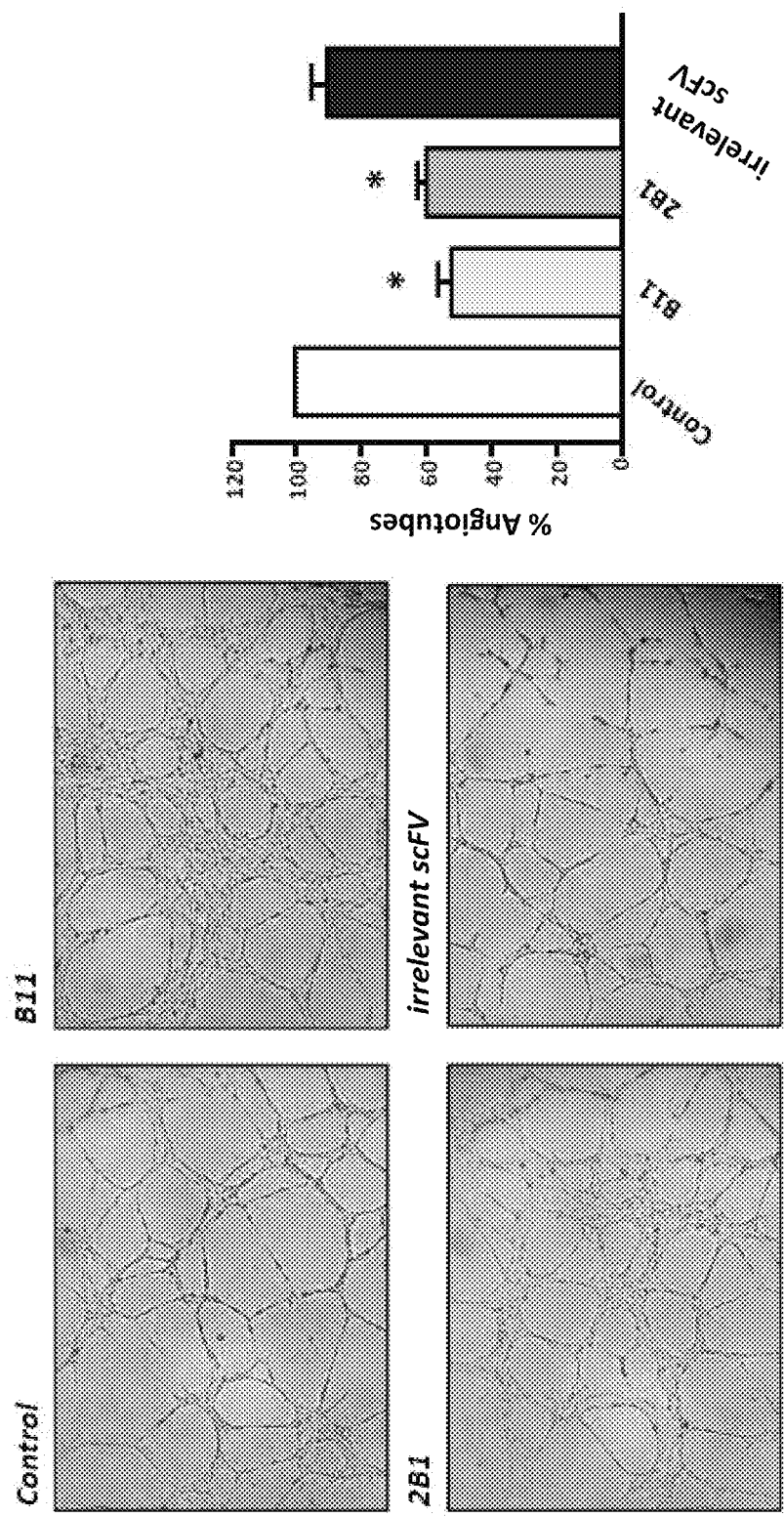
FIG. 6. Inhibitory Effect of B11 and 2B1 on Tubular Structures Formation in vitro by Endothelial Cells HUVEC in Matrigel. Photomicrographs (magnification 4×) representative of tubules formation at 6 hours of cultivate HUVEC cells on Matrigel in the presence of B11, 2B1 or an irrelevant scFv as negative control (C−). As a positive control we used VEGF. The graph shows the quantification of tubules formation. Each treatment was repeated at least three times and corresponding values (mean+/−standard deviation) are plotted as percentage of the tubules formed in the presence of the antibodies tested related to the control without any treatment. *=p<0.0001.

In the experiment of tube formation on Matrigel, it was found that HUVEC cells in the presence of 100 ug/ml of B11 antibody constituted a number of tubules 2-fold lower than in the controls without antibody or with an irrelevant scFv (FIG. 6) and, besides being a decrease in the number of tubules at 6 hours of treatment, there was also a greater disposition of cells in monolayer, it was evidenced that presence of the antibody prevented the formation of tubes. Similar results were obtained with clone 2B1 but with lower inhibition capacity compared to B11, a 40% compared to controls.

Figure 7:
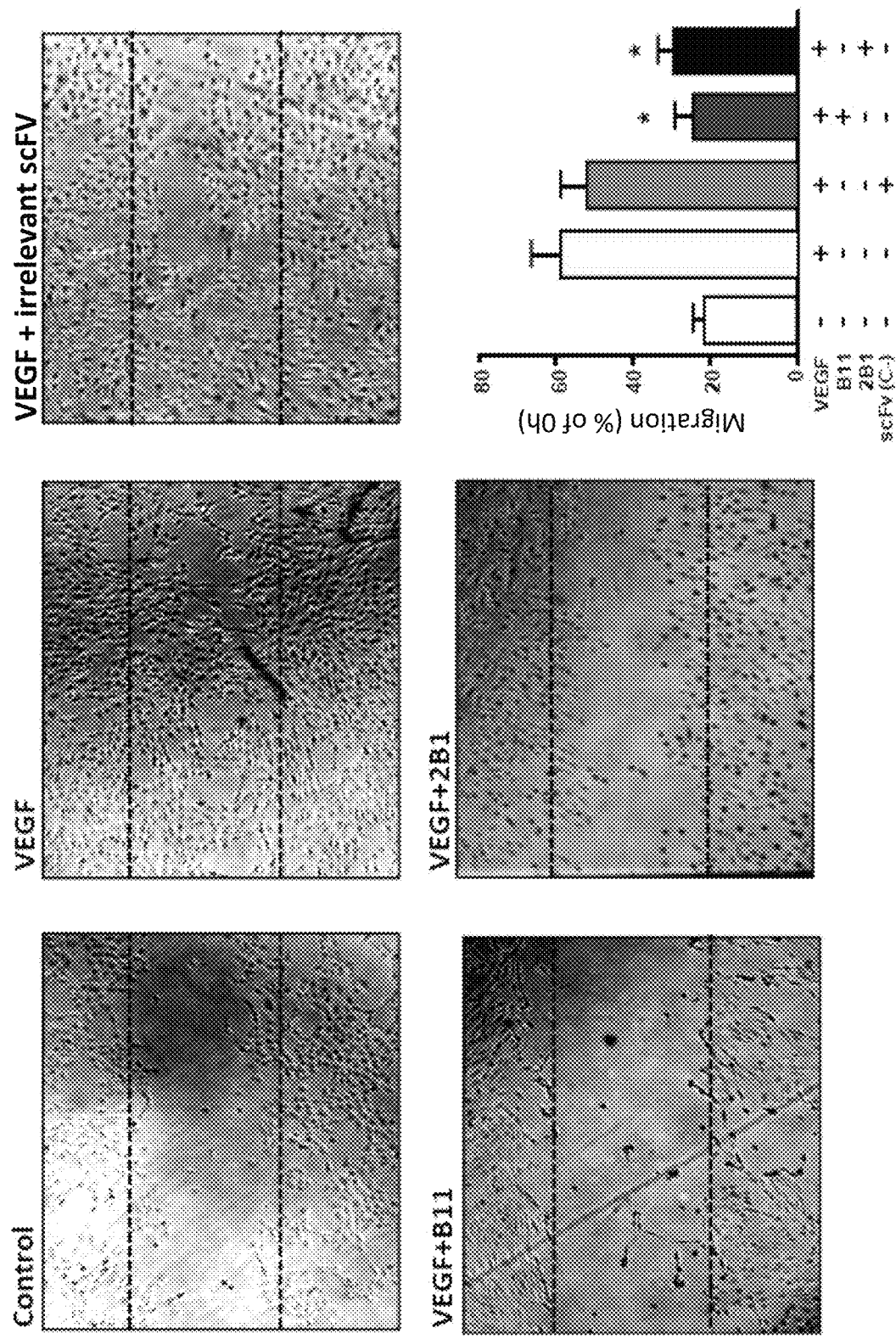
FIG. 7. Analysis of the of Cell Lateral Migration Inhibition by In vitro Wound Healing Assay. HUVEC cells were grown to confluence and a wound was performed in the cell monolayer. Then, cells were incubated in serum free medium in the absence (control) or in presence of VEGF as migration stimulus. The lateral migration of the cells was monitored for 24 hours in the presence of the scFv anti-ephrin B2, B11 or 2B1, or an irrelevant scFv as negative control. The figure shows representative photomicrographs (4× magnification) 24 hours after the wound area on which are marked with dashed lines the initial area without cells at time 0. The graph quantifies cell migration at 24 hours. Each scFv was tested at least three times, and the corresponding values (means+/−standard deviation) were plotted against the percentage of migrated area with respect to time 0. *=p<0.001.

To determine the effect on the lateral migration of HUVEC cells, an experiment in monolayer healing was performed in presence of vascular endothelial growth factor (VEGF) as stimulating agent migration. After 24 hours of making the wound, 60% of the monolayer cells migrated into the free spaces if present VEGF or VEGF and an irrelevant antibody in the process. By contrast, those wounds treated with VEGF and B11 or 2B1, were colonized by only 25% or 30% of cells, respectively, these data are comparable with the number of migrated cells in the negative control (20%) without migration stimulus (FIG. 7).

Therefore, it can be concluded from both experiments that B11 and 2B1 antibodies, and especially the first one, specific for the ephrin B2, exhibit angiogenic capacity and are capable of inhibiting endothelial cell migration in vitro.

Capillary-Shape Structure Formation Assay in Matrigel 24 well plates were coated with Matrigel (BD Biosciences) and incubated at 37° C. for 20 minutes for gelation. Then, HUVEC cells at 5×10$^4$ were plated over the layer of Matrigel in 1 ml of complete medium EGM-2 bullet Kit (Lonza) supplemented with 10% fetal bovine serum, and incubated for 6 hours at 37° C. in presence of different antibodies to 100 μg/ml. At 6 hours was studied the extent of formation of tubular structures by analyzing digital images obtained in a microscope Axiovert 100 (Zeiss) equipped with camera.

Wound Healing Test In vitro

Cell migration assays were performed using in vitro wound healing. HUVEC cells were grown to confluence in 24 well plates, after 1 hour of incubation with EGM-2 (Lonza) supplemented with 0.5% fetal calf serum, it was proceeded to make a linear scraping with a pipette tip and a picture of the area was taken. Cells were incubated in the absence (control conditions) or presence of 100 μg/ml VEGF (Vascular Endothelial Growth Factor, Peprotech) as migration stimuli and 100 μg/ml of the corresponding antibody. After 24 hours turned to take a picture of the area, laterally migrated cells to the wound area were counted and the migrated area percentage was determined from the time the scraping was performed.

Example 3

Figure 8B:
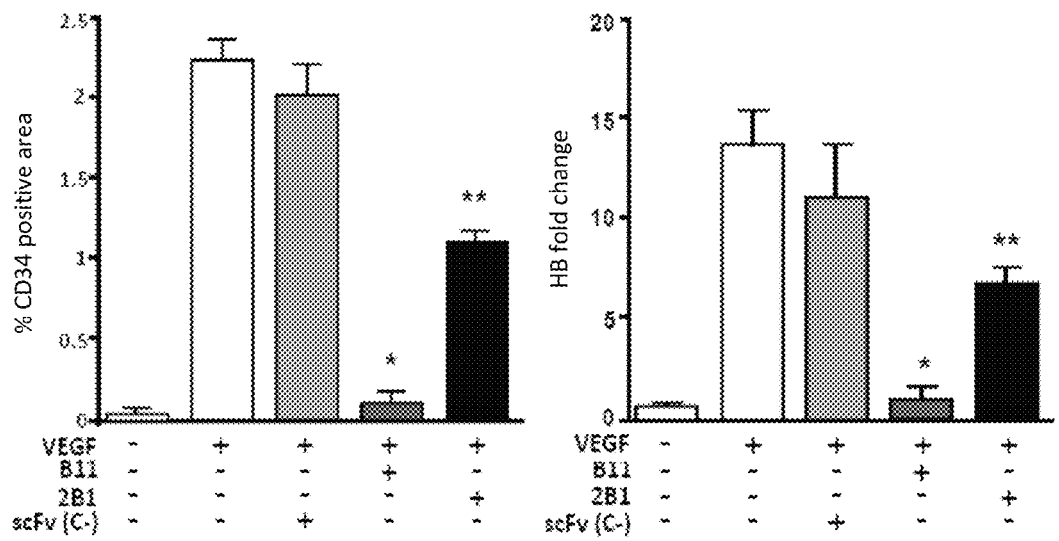
FIG. 8. Analysis of the Inhibitory Effect of Tubular Structures Formation in vivo. Matrigel implants were performed in athymic nu/nu mice and vessels formation were assessed after 6 days of implantation by quantification of endothelial cells and hemoglobin. A. Representative micrographs (magnification 40×) of histological section of the corresponding implants removed after 6 days and stained with the endothelial cell marker CD34. B. The graphs show the percentage of positive area for the marker CD34 (left panel) and the relative change in the hemoglobin content in the implants in relation to control implants without VEGF (right panel).

Effect of B11 and 2B1 Antibodies on Vascularization of Matrigel Implants In vivo In order to demonstrate that the antibodies 2B1 and B11 are capable of directly inhibiting angiogenesis in vivo, it was performed an experiment of Matrigel implants supplemented with VEGF (Peprotech) in athymic nude nu/nu mice, with 6 animals per group. The assessment of the capillary network formation was carried out after 6 days of implantation of the corresponding Matrigel, by quantification of hemoglobin present in the removed implant and by immunohistological staining of CD34, followed by calculation of the positive areas for this blood vessels marker. Treatment with the respective antibodies was started intravenously immediately after implantation of matrigel, on alternate days, until a final dose of 300 μg/mouse. Implants without VEGF were used as negative controls in which did not develop any vascularization (FIG. 8A). By contrast, VEGF implants and implants treated with VEGF and irrelevant scFv showed a prominent vascularisation, considering the positive controls of the experiment. Animals treated with the antibody B11 showed minimal vascularization, a 95% lower than the positive controls, comparable to those presented in the animals implanted with Matrigel without growth factor, which is reflected in a lack of endothelial cells positive for CD34 and hemoglobin in the implants (FIG. 8B). The group of mice treated with the 2B1 antibody showed a 50% inhibition of vessel formation with respect to the positive controls.

Tube Formation Assay In vivo

Athymic nu/nu mice of 4 to 6 weeks old (Charles River) were used. For the control group, the mice anesthetized with 2% isoflurane were injected with 200 μl of Matrigel (BD Biosciences). Another group of animals was injected with 200 μl of Matrigel supplemented with 50 ng/ml VEGF and 375 μg/ml heparin (Sigma) in the upper abdominal region. Immediately after implantation of matrigels, the treatment with scFv intravenously every other day is initiated, until a total dose of 300μ/mouse. After 6 days, the implants were removed and the formation of new vessels was determined according to the concentration of hemoglobin present and in histological sections stained with anti-CD34, a marker of blood vessels. To measure hemoglobin, it was took a portion of each of Matrigel implant, it was weighed and homogenized in 300 μl of distilled water. After centrifugation at 16,000×g for 5 minutes, 100 μl of supernatant were taken and diluted 1:1 with TMB substrate (3,3',5-5'-tetramethylbenzidine) (Sigma). After 15 minutes, the colour reaction is evaluated by measuring optical density at 650 nm. Finally, the values were normalized to the weight of the implant.

For immunohistochemical analysis, portions of the implants were fixed in 10% buffered formalin, embedded in paraffin and sectioned with a microtome to 2.5 μm thick. Antigenic recovery was performed with Tris-EDTA pH 9.0 and endothelial cells were labelled with rat monoclonal anti-CD34 (Abcam) diluted 1:75, followed by a secondary anti-rat antibody labelled with peroxidase (Biocare Medical). Visualization was performed using 3,3-diaminobenzidine tetrahydrochloride plus (DAKO) and counterstained with hematoxylin. The positive cells were counted by the AxioVision system (Zeiss).

Example 4

B11 and 2B1 Antibodies Inhibit the Growth of Human Tumours In Athymic Mice

Given the demonstrated ability of B11 and 2B1 antibodies to affect angiogenesis in vivo and in vitro, it was also studied whether they were also capable of inhibiting a process highly dependent of angiogenesis as tumour growth. For this, three mouse xenograft models with pancreatic carcinoma cells (BxPC3), colorectal (SW620) and lung (H460) were used. The colon and lung cells constitutively express the fluorescent protein mCherry to track tumour progression by analyzing the emitted fluorescence. Previously, it was found that both antibodies, B11 and 2B1, produced no effect on cell viability in vitro in the three cell lines employed.

Figure 9:
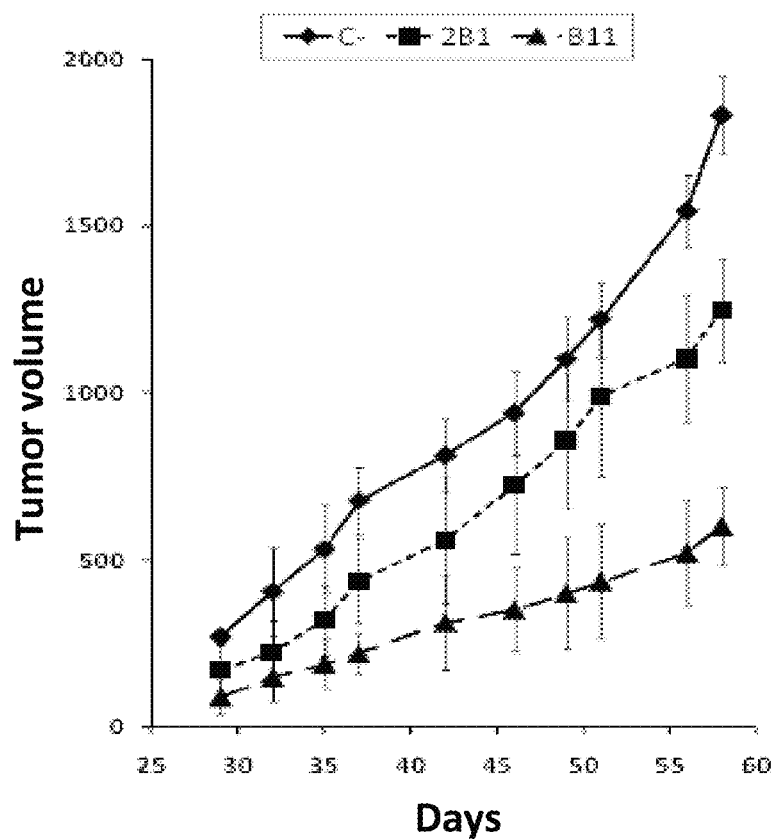
FIG. 9. Inhibition of Tumour Growth in Mice Xenograft with Pancreatic Carcinoma Cells (BxPC3) and Treated with B11 or 2B1. The graph shows the average tumour volumes and standard deviation at each point for each group (n =8) treated with 20 mg/kg of B11 (▲), 2B1 (■) or untreated (C−) (♦).

BxPC3 cells were implanted subcutaneously into 2 groups of 8 mice and once detected macroscopically tumour mass, treatment was initiated intravenously with B11 and 2B1 on alternate days until complete dose of 20 mg/kg or PBS as negative control. After 60 days of implantation of tumour cells was observed that the group of mice treated with the B11 antibody showed a significant reduction of tumour size, a 70% growth inhibition compared with the mean tumour size of the group control (FIG. 9). 2B1-treated mice showed a modest reduction in tumour growth, at around 35%.

Figure 10:
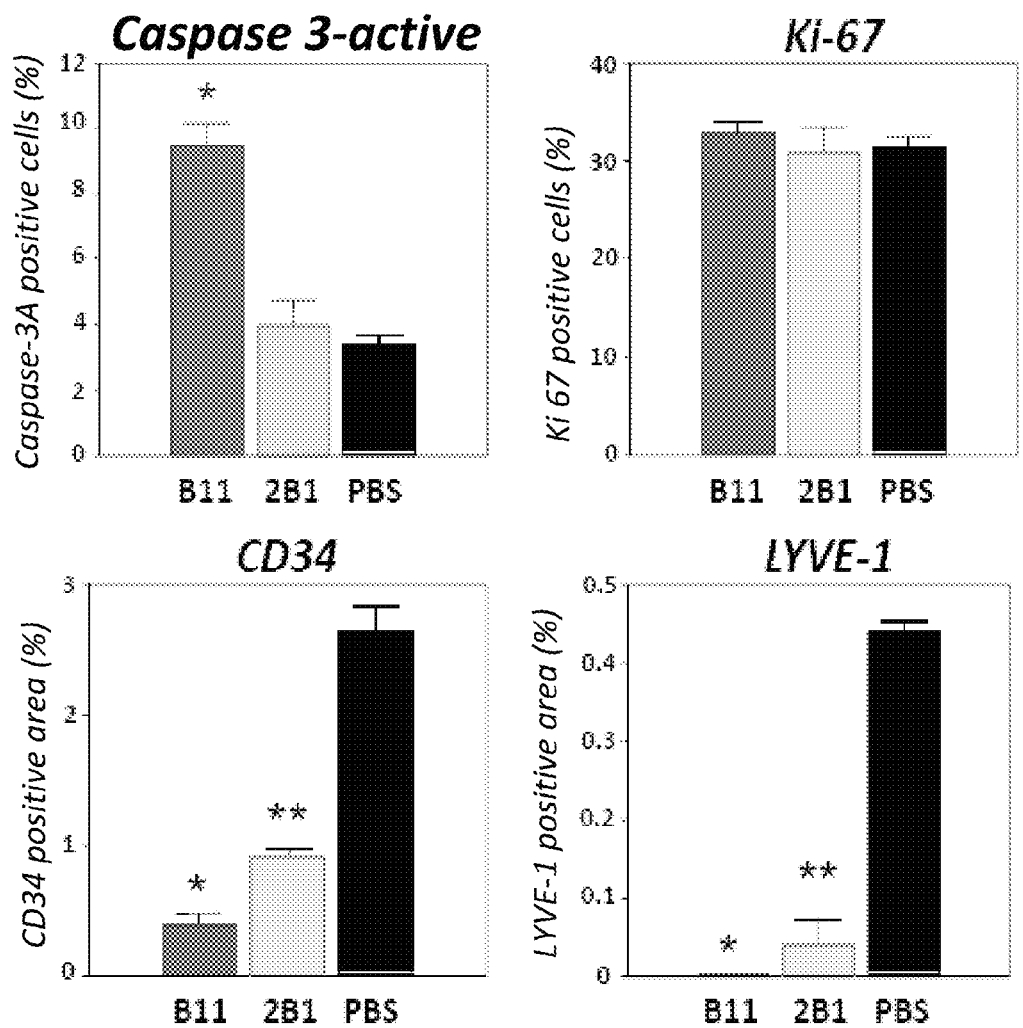
FIG. 10. Histopathological Analysis of Xenograft Tumors Pancreatic Carcinoma Cells (BxPC3) and Treated with B11 or 2B1. The analysis was performed 38 days after implantation and 1 day after the last dose of antibody. Tumours were fixed in formalin and embedded in paraffin for subsequently perform the corresponding immunohistochemical staining.

To study the mechanisms responsible for this inhibition in neoplastic growth, several tumours were removed one day after completion of treatment with the antibody and immunohistochemical analysis was performed to assess the apoptotic status, proliferative, angiogenic and lymphangiogenic with antibodies against caspase 3 active, Ki67, CD34 and Lyve1, respectively (FIG. 10). The number of apoptotic cells in tumours treated with B11 increased 5 times compared to controls. By contrast, the difference between the number of apoptotic cells between the tumors treated with 2B1 and controls was not significant.

Regarding the proliferation marker Ki67, no representative differences between tumours of treated and control animals, showing about 30% of Ki67 positive cells in all three groups.

When analyzed for the presence of blood vessels by measuring the area positive for CD34 in tumours, there was an 80% reduction in tumours treated with B11 with respect to the controls and 55% in the tumours treated with 2B1 with respect to the controls.

Finally, the presence of lymphatic vessels by Lyve1 marker was analyzed, in those treated with B11 tumours was observed almost complete absence of lymphatic vessels. In the tumours treated with 2B1 was also observed a significant decrease in the number of lymphatic vessels, but not as dramatically as in the case of B11.

Figure 11B:
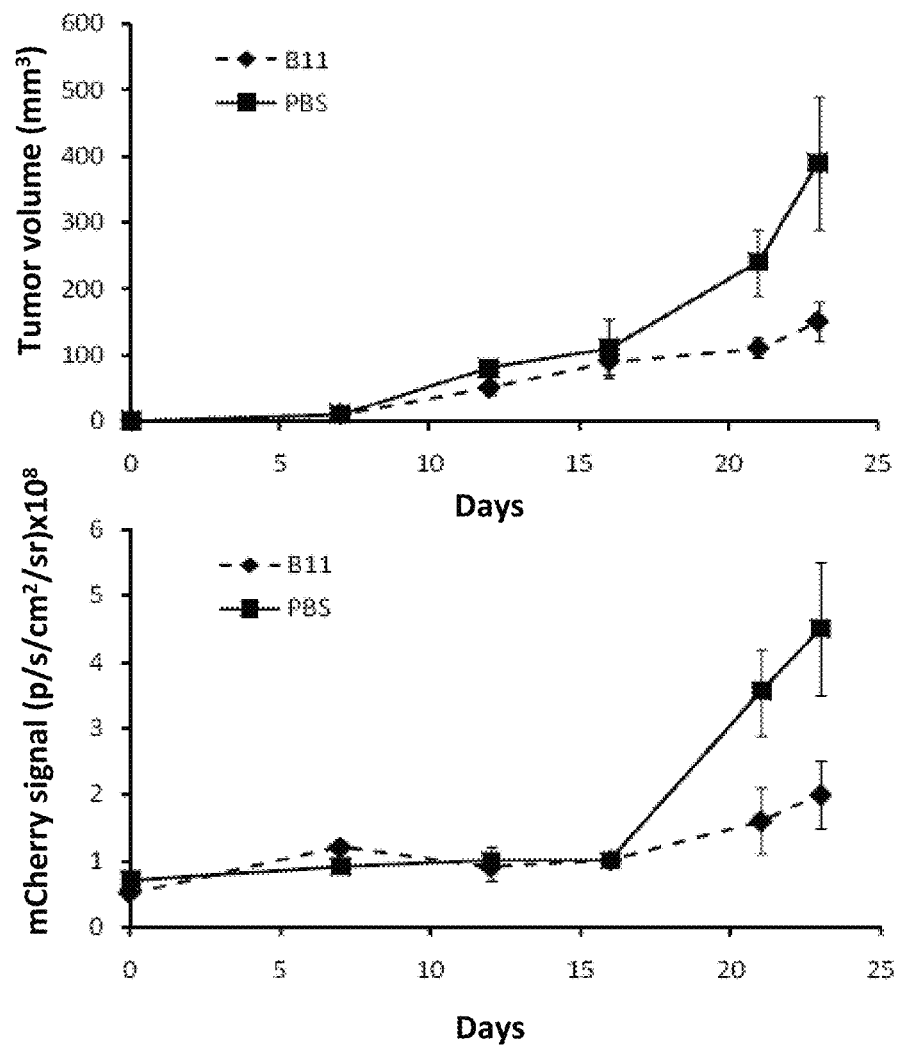

Then, it was studied the antiangiogenic and antilymphangiogenic ability and tumour growth inhibitory capacity of B11 antibody in others xenograft models following the same procedure described above. In the case of cell line SW620 colon carcinoma, it was observed a 90% reduction in tumour size after 23 days after implantation (FIG. 11A), while the reduction in the case of lung cells was 65% (FIG. 11B). This reduction in the respective sizes was verified with a similar decrease in fluorescence emission mCherry protein, present in tumour cells. Immunohistochemical analysis confirmed the decrease in the number of blood vessels and absence of lymphatic vessels in tumours treated with B11, as had been observed in the model of pancreatic carcinoma cells.

Therefore, one can conclude that B11 antibody specific for ephrin B2, has potent antiangiogenic and antilymphangiogenic capacity, which would result in a reduction or delay in the growth of those tumours treated with the antibody. The 2B1 antibody has also a good antiangiogenic and antilymphangiogenic ability.

Xenografts

There were three types of xenografts: with pancreatic carcinoma cells (BxPC3), colorectal (SW620, stably expressing the fluorescent protein mCherry (Clontech) and lung (H460, stably expressing the fluorescent protein mCherry). In all three cases, the same protocol was essentially followed. From 1 to 5 million human tumour cells in a volume of 0.2 ml PBS were injected subcutaneously into the flanks of immunodeficient mice (nude or SCID, "Severe Combined Immunodeficiency") until observe macroscopically a neoplastic mass (approximately 30 mm$^3$). At this time, treatment was started by intravenous administration through the tail veins of the corresponding antibodies in 100-200 µl of PBS on alternate days for 2 weeks or until reaching the final dose of 20 mg/kg. Control animals received PBS following the same guidelines. The sizes of the tumours were measured with a caliper 2-3 times a week and, in the case of mice xenografted with mCherry fluorescent protein labelled cells, fluorescence emission intensity was also measured (number of photons per second and centimeter squared) to 610 nm in an IVIS imaging System Spectrum 200 (Caliper Life Sciences) to display the tumour growth in function of mCherry protein emission intensity. Final processing of the images includes a residual signal subtraction (removal of autofluorescence) and a colour scale following a profile of signal intensity. The animals were sacrificed by $CO_2$ asphyxiation when the tumour reached a predetermined size of 1500-2000 mm$^3$, according to the existing legislation relating to the use of experimental animals. Statistical analysis of tumour growth measurements was performed by parametric analysis using the Student t-test. The statistical significance level was set at $p \leq 0.05$.

Histological Analysis

Tumour samples from xenografted mice were extracted from sacrificed animals one day after completion of treatment with antibodies. The samples were fixed with formalin and embedded in paraffin. Histological sections from each tumour were stained with hematoxylin and eosin or prepared for immunohistochemical characterization. The proliferative activity of tumour cells was analyzed by staining with a monoclonal antibody of rabbit anti-Ki67 (DAKO), the presence of apoptotic cells was detected with a rabbit polyclonal anti-active caspase 3 (R&D), the new vascularisation is measured by staining against CD34 on endothelial cells with a specific rat monoclonal antibody (Abcam) and lymphatic vessels were labelled by staining with a rabbit polyclonal anti-LYVE1 (Abcam). All cuts visualization was carried out with 3,3-diaminobenzidine tetrahydrochloride plus (DAKO) and counterstained with hematoxylin. The positive cells were counted by the AxioVision system (Zeiss).

Example 5

Biodistribution and Location of Tumour Masses In vivo

Figure 12B:
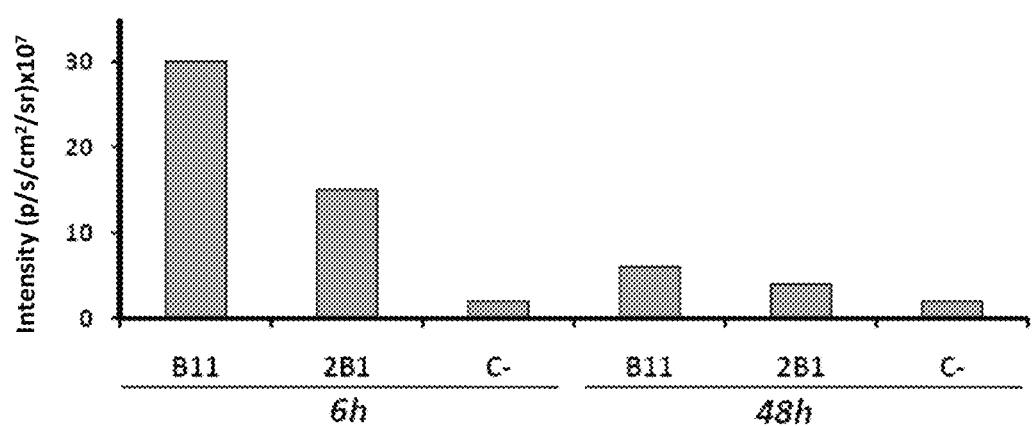

In order to analyze the distribution of the antibody in animals and corroborate the localisation in areas of tumour development, it was designed an experiment in which xenografted mice with a tumour cell line, in this case H460 lung carcinoma, were treated with a fluorochrome labelled Antibody® AlexaFluor 750 (Molecular Probes) which is near-infrared emission. To confirm the position of the tumour mass, cells expressing fluorescent protein mCherry were used. H460 cells were implanted subcutaneously in athymic nude nu/nu mice in the dorsal region. When tumours reached an approximate volume of 0.3 cm$^3$, 15 µg of the antibody conjugated with AlexaFluor® 750 was administered intravenously. At 0.5, 2, 6, 24 and 48 hours after administration, images were taken from the ventral and dorsal regions. The study of mice dorsal images served to locate the antibodies in the tumour mass from the half hour of its administration (FIG. 12A) with a peak at 6 hours (FIG. 12B). The intensity of fluorescence in the tumour emitted by the antibody B11 at 6 hours was clearly superior to that exhibited by the antibody 2B1, indicating that B11 locates more efficiently in the tumour area that 2B1. After half an hour the signal in the bladder and kidneys was very intense, indicating rapid and active elimination of antibodies renally. At 48 hours, the signal was very weak in these areas, with values close to the autofluorescence, suggesting that nearly all of the antibodies had been completely eliminated. Further, the animals showed a fluorescence signal during the first hours in the upper ventral region, attributable to a degree of removal of antibodies by hepatobiliary route, this fact was demonstrated when organs were analyzed separately and it was found that the liver at 6 hours showed a fluorescence of approximately $1 \times 10^8$ p/s/cm$^2$/sr (photons/second/centimeter squared/esterdian).

Biodistribution

For the experiment of scFv distribution, xenografted nude mice were used with the H460 lung carcinoma line stably expressing the mCherry fluorescent protein. The use of cells with fluorescent markers was performed to unambiguously locate the tumour. $5 \times 10^6$ cells were injected subcutaneously and were allowed to grow until the neoplastic mass reached a size of around 500 mm$^3$. Similarly, the scFv were conjugated to the fluorochrome AlexaFluor® 750 by SAIVI™ Rapid Antibody Labeling Kit (Invitrogen) following the manufacturer's instructions. Once the tumours reached the expected size, each mouse was intravenously injected with 15 µg of labelled antibody. The in vivo fluorescence images were taken at 0.5, 2, 6, 24 and 48 hours after administration of scFv labelled with an in vivo imaging system IVIS Spectrum 200 (Caliper Life Sciences) exciting the fluorochrome to 749 nm. After removing the autofluorescence, we proceeded to give a colour scale following a profile of signal intensity.

The invention claimed is:

1. A polypeptide characterized by:
   (a) an amino acid sequence comprising SEQ ID NO: 1;
   (b) specifically recognizes and binds to human ephrin B2; and
   (c) comprising a signal peptide.

2. The polypeptide according to claim 1 wherein said polypeptide is an antibody.

3. The polypeptide according to claim 1 wherein the signal peptide is SEQ ID NO: 6.

4. The polypeptide according to claim 1 characterized by further comprising at least one marker.

5. The polypeptide according to claim 4 wherein the marker is selected from the list comprising: c-myc, FLAG, HA, histidine chain, GST, biotin, VSV-G, HSVtk, V5, biotin, avidin, streptavidin, maltose-binding protein and a fluorescent protein.

6. The polypeptide according to claim 5 wherein the label is a chain of histidines, c-myc or both.

7. A composition comprising the polypeptide according to claim 1.

8. The composition according to claim 7 characterized by further comprising an antiangiogenic agent.

9. The composition according to claim 7 characterized by further comprising a chemotherapeutic agent.

10. The polypeptide according to claim 4 wherein the amino acid sequence of said polypeptide is SEQ ID NO: 7.

* * * * *

SEQUENCE LISTING

<160> NUMBER OF SEQ ID NOS: 8

<210> SEQ ID NO 1
<211> LENGTH: 256
<212> TYPE: PRT
<213> ORGANISM: Homo sapiens

<400> SEQUENCE: 1

Met Ala Gln Val Gln Leu Val Gln Ser Gly Ala Glu Val Lys Lys Pro
1               5                   10                  15

Gly Ala Ser Val Arg Leu Ser Cys Glu Ala Ser Gly Tyr Thr Phe Thr
            20                  25                  30

Asp Tyr Tyr Ile His Trp Val Arg Gln Ala Pro Gly Gln Gly Leu Glu
        35                  40                  45

Trp Met Gly Trp Met Asn Pro Ser Ser Gly Asn Thr Gly Tyr Ala Gln
    50                  55                  60

Lys Phe Gln Gly Arg Val Thr Met Thr Arg Asn Thr Ser Ile Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Asp Ile Thr Gly Thr Ala Thr Gly Phe Asp Tyr Trp
            100                 105                 110

Gly Gln Gly Thr Leu Val Thr Val Ser Ser Gly Gly Gly Ser Gly
        115                 120                 125

Gly Gly Gly Ser Gly Gly Gly Ser Glu Ile Val Leu Thr Gln Ser
    130                 135                 140

Pro Leu Ser Leu Pro Val Thr Leu Gly Gln Pro Ala Ser Ile Ser Cys
145                 150                 155                 160

Arg Ser Ser Gln Ser Leu Leu His Ser Asn Gly Tyr Asn Tyr Leu Asp
                165                 170                 175

Trp Tyr Leu Gln Lys Pro Gly Gln Ser Pro Gln Leu Leu Ile Tyr Leu
            180                 185                 190

Gly Ser Asn Arg Ala Ser Gly Val Pro Asp Arg Phe Ser Gly Ser Gly
        195                 200                 205

Ser Gly Thr Asp Phe Thr Leu Lys Ile Ser Arg Val Glu Ala Glu Asp
    210                 215                 220

Val Gly Val Tyr Tyr Cys Met Gln Gly Leu Leu Ser Pro Val Thr Phe
225                 230                 235                 240

Gly Gln Gly Thr Arg Leu Asp Ile Lys Arg Thr Val Ala Ala Pro Thr
                245                 250                 255

<210> SEQ ID NO 2
<211> LENGTH: 23
<212> TYPE: DNA
<213> ORGANISM: Artificial Sequence
<220> FEATURE:
<223> OTHER INFORMATION: sense primer for verifying the sequence of the
      scFv

<400> SEQUENCE: 2
cataatgaaa tacctattgc cta                                           23

<210> SEQ ID NO 3
<211> LENGTH: 19
<212> TYPE: DNA
<213> ORGANISM: Artificial Sequence
<220> FEATURE:
<223> OTHER INFORMATION: antisense primer for verifying the sequence of
      the scFv

<400> SEQUENCE: 3
cttattagcg tttgccatt                                                           19

<210> SEQ ID NO 4
<211> LENGTH: 28
<212> TYPE: DNA
<213> ORGANISM: Artificial Sequence
<220> FEATURE:
<223> OTHER INFORMATION: sense primer with the RcaI target

<400> SEQUENCE: 4
cagtcatcat gaaataccta ttgcctac                                                 28

<210> SEQ ID NO 5
<211> LENGTH: 28
<212> TYPE: DNA
<213> ORGANISM: Artificial Sequence
<220> FEATURE:
<223> OTHER INFORMATION: antisense primer with the XhoI target

<400> SEQUENCE: 5
caccggactc gagtgcggcc ccattcag                                                 28

<210> SEQ ID NO 6
<211> LENGTH: 20
<212> TYPE: PRT
<213> ORGANISM: Erwinia carotovora

<400> SEQUENCE: 6

Met Lys Tyr Leu Leu Pro Thr Ala Ala Ala Gly Leu Leu Leu Leu Ala
1               5                   10                  15

Ala Gln Pro Ala
            20

<210> SEQ ID NO 7
<211> LENGTH: 301
<212> TYPE: PRT
<213> ORGANISM: Artificial Sequence
<220> FEATURE:
<223> OTHER INFORMATION: scFv from clon B11 including signal peptide,
      c-myc, and histidine chain

<400> SEQUENCE: 7

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Ala Glu
            20                  25                  30

Val Lys Lys Pro Gly Ala Ser Val Arg Leu Ser Cys Glu Ala Ser Gly
        35                  40                  45

Tyr Thr Phe Thr Asp Tyr Tyr Ile His Trp Val Arg Gln Ala Pro Gly
    50                  55                  60

Gln Gly Leu Glu Trp Met Gly Trp Met Asn Pro Ser Ser Gly Asn Thr
65                  70                  75                  80

Gly Tyr Ala Gln Lys Phe Gln Gly Arg Val Thr Met Thr Arg Asn Thr
                85                  90                  95

Ser Ile Ser Thr Ala Tyr Met Glu Leu Ser Ser Leu Arg Ser Glu Asp
            100                 105                 110

Thr Ala Val Tyr Tyr Cys Ala Arg Asp Ile Thr Gly Thr Ala Thr Gly
        115                 120                 125

Phe Asp Tyr Trp Gly Gln Gly Thr Leu Val Thr Val Ser Ser Gly Gly

```
                            130                 135                 140
Gly Gly Ser Gly Gly Gly Ser Gly Gly Gly Ser Glu Ile Val
145                 150                 155                 160

Leu Thr Gln Ser Pro Leu Ser Leu Pro Val Thr Leu Gly Gln Pro Ala
                        165                 170                 175

Ser Ile Ser Cys Arg Ser Ser Gln Ser Leu Leu His Ser Asn Gly Tyr
                180                 185                 190

Asn Tyr Leu Asp Trp Tyr Leu Gln Lys Pro Gly Gln Ser Pro Gln Leu
                195                 200                 205

Leu Ile Tyr Leu Gly Ser Asn Arg Ala Ser Gly Val Pro Asp Arg Phe
        210                 215                 220

Ser Gly Ser Gly Ser Gly Thr Asp Phe Thr Leu Lys Ile Ser Arg Val
225                 230                 235                 240

Glu Ala Glu Asp Val Gly Val Tyr Tyr Cys Met Gln Gly Leu Leu Ser
                245                 250                 255

Pro Val Thr Phe Gly Gln Gly Thr Arg Leu Asp Ile Lys Arg Thr Val
                260                 265                 270

Ala Ala Pro Thr Ala Ala Ala Glu Gln Lys Leu Ile Ser Glu Glu Asp
        275                 280                 285

Leu Asn Gly Ala Ala Leu Glu His His His His His
        290                 295                 300

<210> SEQ ID NO 8
<211> LENGTH: 291
<212> TYPE: PRT
<213> ORGANISM: Artificial Sequence
<220> FEATURE:
<223> OTHER INFORMATION: scFv from clon 2B1

<400> SEQUENCE: 8

Met Lys Tyr Leu Leu Pro Thr Ala Ala Ala Gly Leu Leu Leu Leu Ala
1               5                   10                  15

Ala Gln Pro Ala Met Ala Gln Val Gln Leu Val Gln Ser Gly Gly Gly
                20                  25                  30

Leu Val Gln Pro Gly Arg Ser Leu Arg Leu Ser Cys Ala Ala Ser Gly
            35                  40                  45

Phe Thr Phe Asp Asp Tyr Ala Met His Trp Val Arg Gln Ala Pro Gly
        50                  55                  60

Lys Gly Leu Glu Trp Val Ser Gly Ile Ser Trp Asn Ser Gly Ser Ile
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Leu Tyr Tyr Cys Ala Arg Gly His Arg Thr Ser Asp Ala Phe
        115                 120                 125

Asp Ile Trp Gly Gln Gly Thr Met Val Thr Val Ser Ser Gly Gly Gly
    130                 135                 140

Gly Ser Gly Gly Gly Gly Ser Gly Gly Gly Ser Gln Pro Val Leu
145                 150                 155                 160

Thr Gln Pro Pro Ser Val Ser Leu Ala Pro Gly Lys Thr Ala Arg Ile
                165                 170                 175

Thr Cys Gly Gly Asp Ser Ile Gly Leu Lys Ser Val His Trp Tyr Gln
            180                 185                 190

Gln Lys Pro Gly Gln Ala Pro Val Leu Val Met Ser Ser Asp Ser Asp
```

-continued

```
            195                 200                 205
Arg Pro Ser Gly Ile Pro Asp Arg Phe Ser Gly Ser Asn Ser Gly Asn
        210                 215                 220

Thr Ala Thr Leu Thr Ile Thr Arg Val Glu Ala Gly Asp Glu Ala Asp
225                 230                 235                 240

Tyr Tyr Cys Gln Val Trp Asp Ser Ser Asp His Met Val Phe Gly
                245                 250                 255

Gly Gly Thr Lys Leu Thr Val Leu Gly Gln Pro Lys Ala Ala Pro Ser
            260                 265                 270

Ala Ala Ala Leu Glu Asp Tyr Lys Asp Asp Asp Asp Lys His His His
        275                 280                 285

His His His
    290
```